US012751829B2

(12) United States Patent
Viscardi et al.

(10) Patent No.: US 12,751,829 B2
(45) Date of Patent: Oct. 6, 2026

(54) IMPLANTS WITH MODULAR STEMS WITH TENSION/COMPRESSION MECHANISMS

(71) Applicant: WRIGHT MEDICAL TECHNOLOGY, INC., Memphis, TN (US)

(72) Inventors: David Charles Viscardi, Glen Rock, NJ (US); Terrance W. Strohkirch, Memphis, TN (US); Jerry W. West, Arlington, TN (US); Jesse G. Moore, Germantown, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 622 days.

(21) Appl. No.: 18/352,402

(22) Filed: Jul. 14, 2023

(65) Prior Publication Data

US 2024/0099853 A1 Mar. 28, 2024

Related U.S. Application Data

(60) Provisional application No. 63/377,423, filed on Sep. 28, 2022.

(51) Int. Cl.
*A61F 2/38* (2006.01)
*A61F 2/30* (2006.01)

(52) U.S. Cl.
CPC .... *A61F 2/389* (2013.01); *A61F 2002/30332* (2013.01); *A61F 2002/30408* (2013.01);
(Continued)

(58) Field of Classification Search
CPC ................ A61F 2/4202; A61F 2/30724; A61F 2/30749; A61F 2/30734;
(Continued)

(56) References Cited

U.S. PATENT DOCUMENTS

| | | | |
|---|---|---|---|
| 3,314,420 | A | 4/1967 | Smith et al. |
| 3,605,123 | A | 9/1971 | Hahn |

(Continued)

FOREIGN PATENT DOCUMENTS

| | | |
|---|---|---|
| CN | 1662186 | 8/2005 |
| CN | 101111197 | 1/2008 |

(Continued)

OTHER PUBLICATIONS

Extended European Search Report issued in connection with corresponding European Patent Application No. 23187086.6, Feb. 14, 2024, 8 pages.

(Continued)

*Primary Examiner* — Javier G Blanco
(74) *Attorney, Agent, or Firm* — DUANE MORRIS LLP

(57) ABSTRACT

A prosthesis may include a first component, a second component, and a coupling member. The first component may include a first body extending from a first end to a second end, which may define a first opening that extends inwardly toward the first end. The first opening may include a first portion having a first diameter and a second portion having a second diameter. The second component may include a second body extending from a first end to a second end. The second body may define a second opening that extends through the second body. The coupling member may be configured to couple the first component and the second component by compressing the first component and the second component. The coupling member may include a shaft portion and a head portion. The shaft portion may be sized and configured to be received in the first opening and the second opening.

22 Claims, 14 Drawing Sheets

(52) U.S. Cl.
CPC ............... *A61F 2002/30604* (2013.01); *A61F 2002/30822* (2013.01); *A61F 2002/3093* (2013.01)

(58) Field of Classification Search
CPC .. A61F 2002/30736; A61F 2002/30332; A61F 2002/30599; A61F 2002/30604; A61F 2002/30507; A61F 2002/30827; A61F 2002/30822; A61F 2/6607
See application file for complete search history.

(56) References Cited

U.S. PATENT DOCUMENTS 3,708,883 A 1/1973 Flander
3,798,679 A 3/1974 Ewald
3,808,606 A 5/1974 Tronzo
3,843,975 A 10/1974 Tronzo
3,855,638 A 12/1974 Pilliar
3,938,198 A 2/1976 Kahn et al.
3,987,499 A 10/1976 Scharbach et al.
4,052,753 A 10/1977 Dedo
4,055,862 A 11/1977 Farling
4,085,466 A 4/1978 Goodfellow et al.
4,098,626 A 7/1978 Graham et al.
4,203,444 A 5/1980 Bonnell et al.
4,213,816 A 7/1980 Morris
4,340,978 A 7/1982 Buechel et al.
4,368,040 A 1/1983 Weissman
4,436,684 A 3/1984 White
4,501,266 A 2/1985 McDaniel
4,502,161 A 3/1985 Wall
4,578,806 A 3/1986 Grass et al.
4,586,496 A 5/1986 Keller
4,594,380 A 6/1986 Chapin et al.
4,601,290 A 7/1986 Effron et al.
4,609,551 A 9/1986 Caplan et al.
4,627,853 A 12/1986 Campbell et al.
4,703,751 A 11/1987 Pohl
4,704,686 A 11/1987 Aldinger
4,715,860 A 12/1987 Amstutz et al.
4,721,104 A 1/1988 Kaufman et al.
4,759,350 A 7/1988 Dunn et al.
4,769,040 A 9/1988 Wevers
4,841,975 A 6/1989 Woolson
4,846,835 A 7/1989 Grande
4,865,607 A 9/1989 Witzel et al.
4,880,429 A 11/1989 Stone
4,936,862 A 6/1990 Walker et al.
4,979,949 A 12/1990 Matsen, III et al.
5,002,547 A 3/1991 Poggie
5,041,138 A 8/1991 Vacanti et al.
5,059,216 A 10/1991 Winters
5,067,964 A 11/1991 Richmond et al.
5,122,144 A 6/1992 Bert et al.
5,129,908 A 7/1992 Petersen
5,133,759 A 7/1992 Turner
5,154,717 A 10/1992 Matsen, III et al.
5,162,430 A 11/1992 Rhee et al.
5,171,322 A 12/1992 Kenny
5,197,985 A 3/1993 Caplan et al.
5,206,023 A 4/1993 Hunziker
5,226,914 A 7/1993 Caplan et al.
5,234,433 A 8/1993 Bert et al.
5,250,050 A 10/1993 Poggie et al.
5,258,032 A 11/1993 Bertin
5,270,300 A 12/1993 Hunziker
5,288,797 A 2/1994 Khalil et al.
5,303,148 A 4/1994 Mattson et al.
5,306,311 A 4/1994 Stone et al.
5,314,482 A 5/1994 Goodfellow et al.
5,344,459 A 9/1994 Swartz
5,360,446 A 11/1994 Kennedy
5,365,996 A 11/1994 Crook
5,368,858 A 11/1994 Hunziker
5,370,692 A 12/1994 Fink et al.
5,380,332 A 1/1995 Ferrante
5,387,216 A 2/1995 Thornhill et al.
5,454,816 A 10/1995 Ashby
5,462,550 A 10/1995 Dietz et al.
5,468,787 A 11/1995 Braden et al.
5,474,559 A 12/1995 Bertin et al.
5,478,739 A 12/1995 Slivka et al.
5,486,180 A 1/1996 Dietz et al.
5,501,687 A 3/1996 Willert et al.
5,503,162 A 4/1996 Athanasiou et al.
5,520,695 A 5/1996 Luckman
5,523,843 A 6/1996 Yamane et al.
5,540,696 A 7/1996 Booth, Jr. et al.
5,542,947 A 8/1996 Treacy
5,554,190 A 9/1996 Draenert
5,556,432 A 9/1996 Kubein-Meesenburg et al.
5,571,205 A 11/1996 James
5,575,793 A 11/1996 Carls et al.
5,578,037 A 11/1996 Sanders et al.
5,593,450 A 1/1997 Scott et al.
5,597,379 A 1/1997 Haines et al.
5,601,563 A 2/1997 Burke et al.
5,613,970 A 3/1997 Houston et al.
5,616,146 A 4/1997 Murray
5,630,820 A 5/1997 Todd
5,632,745 A 5/1997 Schwartz
5,649,929 A 7/1997 Callaway
5,658,290 A 8/1997 Techeira
5,671,741 A 9/1997 Lang et al.
5,682,886 A 11/1997 Delp et al.
5,683,466 A 11/1997 Vitale
5,684,562 A 11/1997 Fujieda
5,688,282 A 11/1997 Baron et al.
5,702,445 A * 12/1997 Brånemark ......... A61F 2/30721 411/421
5,728,162 A 3/1998 Eckhoff
5,735,277 A 4/1998 Schuster
5,749,874 A 5/1998 Schwartz
5,749,876 A 5/1998 Duvillier et al.
5,765,561 A 6/1998 Chen et al.
5,768,134 A 6/1998 Swaelens et al.
5,769,899 A 6/1998 Schwartz et al.
5,782,842 A 7/1998 Kloess et al.
5,786,217 A 7/1998 Tuba et al.
5,798,924 A 8/1998 Eufinger et al.
5,800,438 A 9/1998 Tuke et al.
5,824,083 A 10/1998 Draenert
5,827,289 A 10/1998 Reiley et al.
5,830,216 A 11/1998 Insall et al.
5,835,619 A 11/1998 Morimoto et al.
5,842,477 A 12/1998 Naughton et al.
5,847,804 A 12/1998 Sarver et al.
5,853,746 A 12/1998 Hunziker
5,860,981 A 1/1999 Bertin et al.
5,871,018 A 2/1999 Delp et al.
5,871,542 A 2/1999 Goodfellow et al.
5,871,546 A 2/1999 Colleran et al.
5,879,390 A 3/1999 Kubein-Meesenburg et al.
5,880,976 A 3/1999 DiGioia, III et al.
5,885,296 A 3/1999 Masini
5,885,297 A 3/1999 Matsen, III
5,885,298 A 3/1999 Herrington et al.
5,897,559 A 4/1999 Masini
5,899,859 A 5/1999 Votruba et al.
5,900,245 A 5/1999 Sawhney et al.
5,906,934 A 5/1999 Grande et al.
5,911,723 A 6/1999 Ashby et al.
5,916,220 A 6/1999 Masini
5,916,268 A 6/1999 Schollner et al.
5,939,323 A 8/1999 Valentini et al.
5,951,475 A 9/1999 Gueziec et al.
5,961,523 A 10/1999 Masini
5,968,051 A 10/1999 Luckman et al.
5,972,385 A 10/1999 Liu et al.
5,995,738 A 11/1999 DiGioia, III et al.
6,001,895 A 12/1999 Harvey et al.
6,002,859 A 12/1999 DiGioia, III et al.
6,006,126 A 12/1999 Cosman
6,007,537 A 12/1999 Burkinshaw et al.

(56) References Cited

U.S. PATENT DOCUMENTS 6,010,509 A 1/2000 Delgado et al.
6,013,081 A 1/2000 Burkinshaw et al.
6,013,103 A 1/2000 Kaufman et al.
6,046,379 A 4/2000 Stone et al.
6,056,754 A 5/2000 Haines et al.
6,056,756 A 5/2000 Eng et al.
6,057,927 A 5/2000 Levesque et al.
6,077,270 A 6/2000 Katz
6,082,364 A 7/2000 Balian et al.
6,090,144 A 7/2000 Letot et al.
6,093,204 A 7/2000 Stone
6,096,043 A 8/2000 Techiera et al.
6,102,916 A 8/2000 Masini
6,106,529 A 8/2000 Techiera
6,110,209 A 8/2000 Stone
6,120,541 A 9/2000 Johnson
6,126,690 A 10/2000 Ateshian et al.
6,139,578 A 10/2000 Lee et al.
6,156,069 A 12/2000 Amstutz
6,161,080 A 12/2000 Aouni-Ateshian et al.
6,187,010 B1 2/2001 Masini
6,200,606 B1 3/2001 Peterson et al.
6,203,546 B1 3/2001 MacMahon
6,203,576 B1 3/2001 Afriat et al.
6,205,411 B1 3/2001 DiGioia, III et al.
6,206,927 B1 3/2001 Fell et al.
6,214,369 B1 4/2001 Grande et al.
6,217,894 B1 4/2001 Sawhney et al.
6,219,571 B1 4/2001 Hargreaves et al.
6,224,632 B1 5/2001 Pappas et al.
6,235,060 B1 5/2001 Kubein-Meesenburg et al.
6,251,143 B1 6/2001 Schwartz et al.
6,254,639 B1 7/2001 Peckitt
6,277,151 B1 8/2001 Lee et al.
6,281,195 B1 8/2001 Rueger et al.
6,283,980 B1 9/2001 Vibe-Hansen et al.
6,296,646 B1 10/2001 Williamson
6,299,905 B1 10/2001 Peterson et al.
6,322,588 B1 11/2001 Ogle et al.
6,327,491 B1 12/2001 Franklin et al.
6,328,765 B1 12/2001 Hardwick et al.
6,344,043 B1 2/2002 Pappas
6,344,059 B1 2/2002 Krakovits et al.
6,352,558 B1 3/2002 Spector
6,358,253 B1 3/2002 Torrie et al.
6,365,405 B1 4/2002 Salzmann et al.
6,371,958 B1 4/2002 Overaker
6,373,250 B1 4/2002 Tsoref et al.
6,375,658 B1 4/2002 Hangody et al.
6,379,367 B1 4/2002 Vibe-Hansen et al.
6,382,028 B1 5/2002 Wooh et al.
6,383,228 B1 5/2002 Schmotzer
6,387,131 B1 5/2002 Miehlke et al.
6,409,767 B1 6/2002 Perice et al.
6,429,013 B1 8/2002 Halvorsen et al.
6,443,988 B2 9/2002 Felt et al.
6,443,991 B1 9/2002 Running
6,444,222 B1 9/2002 Asculai et al.
6,459,927 B1 10/2002 Franklin et al.
6,459,948 B1 10/2002 Ateshian et al.
6,468,314 B2 10/2002 Schwartz et al.
6,478,799 B1 11/2002 Williamson
6,479,996 B1 11/2002 Hoogeveen et al.
6,510,334 B1 1/2003 Schuster et al.
6,520,964 B2 2/2003 Tallarida et al.
6,558,421 B1 5/2003 Fell et al.
6,560,476 B1 5/2003 Pelletier et al.
6,575,980 B1 6/2003 Robie et al.
6,610,099 B1 * 8/2003 Albrektsson .......... A61F 2/3601
623/23.11
6,620,168 B1 9/2003 Lombardo et al.
6,626,945 B2 9/2003 Simon et al.
6,626,948 B2 9/2003 Storer et al.
6,632,225 B2 10/2003 Sanford et al.
6,632,235 B2 10/2003 Weikel et al.
6,652,587 B2 11/2003 Felt et al.
6,673,077 B1 1/2004 Katz
6,679,917 B2 1/2004 Ek
6,712,856 B1 3/2004 Carignan et al.
6,738,657 B1 5/2004 Franklin et al.
6,905,514 B2 6/2005 Carignan et al.
6,916,341 B2 7/2005 Rolston
6,928,742 B2 8/2005 Broers et al.
6,932,842 B1 8/2005 Litschko et al.
6,942,667 B1 9/2005 Song
6,944,518 B2 9/2005 Roose
6,969,393 B2 11/2005 Pinczewski et al.
6,980,849 B2 12/2005 Sasso
6,988,015 B1 1/2006 Schopf et al.
6,993,374 B2 1/2006 Sasso
7,008,430 B2 3/2006 Dong et al.
7,058,439 B2 6/2006 Eaton et al.
7,060,074 B2 6/2006 Rosa et al.
7,104,997 B2 9/2006 Lionberger et al.
7,115,131 B2 10/2006 Engh et al.
7,117,027 B2 10/2006 Zheng et al.
7,141,053 B2 11/2006 Rosa et al.
7,153,326 B1 12/2006 Metzger
7,184,814 B2 2/2007 Lang et al.
7,201,762 B2 4/2007 Green, Jr. et al.
7,217,276 B2 5/2007 Henderson et al.
7,239,908 B1 7/2007 Alexander et al.
7,245,697 B2 7/2007 Lang
7,282,054 B2 10/2007 Steffensmeier et al.
7,292,674 B2 11/2007 Lang
7,347,690 B2 3/2008 Jordan et al.
7,364,581 B2 4/2008 Michalowicz
7,377,924 B2 5/2008 Raistrick et al.
7,379,529 B2 5/2008 Lang
7,467,892 B2 12/2008 Lang et al.
7,468,075 B2 12/2008 Lang et al.
7,534,246 B2 5/2009 Reiley et al.
7,534,263 B2 5/2009 Burdulis, Jr. et al.
7,618,451 B2 11/2009 Berez et al.
7,747,305 B2 6/2010 Dean et al.
7,806,896 B1 10/2010 Bonutti
7,881,768 B2 2/2011 Lang et al.
7,914,533 B2 3/2011 Nelson et al.
7,981,158 B2 7/2011 Fitz et al.
7,983,777 B2 7/2011 Melton et al.
8,036,729 B2 10/2011 Lang et al.
8,062,302 B2 11/2011 Lang et al.
8,066,708 B2 11/2011 Lang et al.
8,083,745 B2 12/2011 Lang et al.
8,105,330 B2 1/2012 Fitz et al.
8,112,142 B2 2/2012 Alexander et al.
8,122,592 B2 2/2012 Burdulis, Jr. et al.
RE43,282 E 3/2012 Alexander et al.
8,430,879 B2 4/2013 Stoneburner et al.
8,496,663 B2 7/2013 White et al.
8,535,319 B2 9/2013 Ball
8,579,980 B2 11/2013 Delurio et al.
8,715,362 B2 * 5/2014 Reiley .................... A61B 17/15
623/23.44
8,808,297 B2 8/2014 Stemniski
8,808,303 B2 8/2014 Stemniski
9,017,334 B2 4/2015 Carroll et al.
9,125,674 B2 9/2015 White et al.
9,128,627 B1 9/2015 Bachu et al.
9,259,250 B2 2/2016 Saravia et al.
9,265,511 B2 2/2016 White et al.
9,402,640 B2 8/2016 Stemniski et al.
9,672,607 B2 6/2017 Demri et al.
10,105,168 B2 10/2018 Blau
10,130,430 B2 11/2018 Kao et al.
10,390,842 B2 8/2019 Sander
10,413,308 B2 9/2019 Stemniski et al.
10,433,911 B2 10/2019 Wang et al.
10,456,179 B2 10/2019 Luna et al.
10,667,867 B2 6/2020 Ashish et al.
10,835,265 B2 11/2020 White et al.
10,835,266 B2 11/2020 White et al.
11,147,627 B2 10/2021 Gangwar et al.
11,172,945 B1 11/2021 Lian

(56) References Cited

U.S. PATENT DOCUMENTS

| | | | |
|---|---|---|---|
| 2001/0001120 | A1 | 5/2001 | Masini |
| 2001/0010023 | A1 | 7/2001 | Schwartz et al. |
| 2001/0039455 | A1 | 11/2001 | Simon et al. |
| 2002/0013626 | A1 | 1/2002 | Geisllich et al. |
| 2002/0029038 | A1 | 3/2002 | Haines |
| 2002/0045940 | A1 | 4/2002 | Giannelli et al. |
| 2002/0059049 | A1 | 5/2002 | Bradbury et al. |
| 2002/0068979 | A1 | 6/2002 | Brown et al. |
| 2002/0072821 | A1 | 6/2002 | Baker |
| 2002/0079601 | A1 | 6/2002 | Russell et al. |
| 2002/0082703 | A1 | 6/2002 | Repicci |
| 2002/0087274 | A1 | 7/2002 | Alexander et al. |
| 2002/0106625 | A1 | 8/2002 | Hung et al. |
| 2002/0115647 | A1 | 8/2002 | Halvorsen et al. |
| 2002/0120274 | A1 | 8/2002 | Overaker et al. |
| 2002/0120281 | A1 | 8/2002 | Overaker |
| 2002/0123817 | A1 | 9/2002 | Clasbrummel et al. |
| 2002/0127264 | A1 | 9/2002 | Felt et al. |
| 2002/0133230 | A1 | 9/2002 | Repicci |
| 2002/0143402 | A1 | 10/2002 | Steinberg |
| 2002/0151986 | A1 | 10/2002 | Asculai et al. |
| 2002/0156150 | A1 | 10/2002 | Asculai et al. |
| 2002/0156479 | A1 | 10/2002 | Schulzki et al. |
| 2002/0173852 | A1 | 11/2002 | Felt et al. |
| 2002/0183850 | A1 | 12/2002 | Felt et al. |
| 2002/0198531 | A1 | 12/2002 | Millard et al. |
| 2003/0028196 | A1 | 2/2003 | Bonutti |
| 2003/0055500 | A1 | 3/2003 | Fell et al. |
| 2003/0055501 | A1 | 3/2003 | Fell et al. |
| 2003/0055502 | A1 | 3/2003 | Lang et al. |
| 2003/0060882 | A1 | 3/2003 | Fell et al. |
| 2003/0060883 | A1 | 3/2003 | Fell et al. |
| 2003/0060884 | A1 | 3/2003 | Fell et al. |
| 2003/0060885 | A1 | 3/2003 | Fell et al. |
| 2003/0100907 | A1 | 5/2003 | Rosa et al. |
| 2003/0100953 | A1 | 5/2003 | Rosa et al. |
| 2003/0120347 | A1 | 6/2003 | Steinberg |
| 2003/0158558 | A1 | 8/2003 | Horn |
| 2003/0158606 | A1 | 8/2003 | Coon et al. |
| 2003/0163137 | A1 | 8/2003 | Smucker et al. |
| 2003/0173695 | A1 | 9/2003 | Monkhouse et al. |
| 2003/0216669 | A1 | 11/2003 | Lang et al. |
| 2003/0225457 | A1 | 12/2003 | Justin et al. |
| 2003/0236521 | A1 | 12/2003 | Brown et al. |
| 2003/0236526 | A1 | 12/2003 | Van Hoeck et al. |
| 2004/0098133 | A1 | 5/2004 | Carignan et al. |
| 2004/0102852 | A1 | 5/2004 | Johnson et al. |
| 2004/0122521 | A1 | 6/2004 | Lee et al. |
| 2004/0133276 | A1 | 7/2004 | Lang et al. |
| 2004/0138754 | A1 | 7/2004 | Lang et al. |
| 2004/0147927 | A1 | 7/2004 | Tsougarakis et al. |
| 2004/0153079 | A1 | 8/2004 | Tsougarakis et al. |
| 2004/0153162 | A1 | 8/2004 | Sanford et al. |
| 2004/0153164 | A1 | 8/2004 | Sanford et al. |
| 2004/0167390 | A1 | 8/2004 | Alexander et al. |
| 2004/0167630 | A1 | 8/2004 | Rolston |
| 2004/0193268 | A1 | 9/2004 | Hazebrouck et al. |
| 2004/0193280 | A1 | 9/2004 | Webster et al. |
| 2004/0199166 | A1 | 10/2004 | Schmieding et al. |
| 2004/0204644 | A1 | 10/2004 | Tsougarakis et al. |
| 2004/0204760 | A1 | 10/2004 | Fitz et al. |
| 2004/0236424 | A1 | 11/2004 | Berez et al. |
| 2004/0249386 | A1 | 12/2004 | Faoro |
| 2005/0015153 | A1 | 1/2005 | Goble et al. |
| 2005/0021039 | A1 | 1/2005 | Cusick et al. |
| 2005/0043807 | A1 | 2/2005 | Wood |
| 2005/0049603 | A1 | 3/2005 | Calton et al. |
| 2005/0055028 | A1 | 3/2005 | Haines |
| 2005/0085920 | A1 | 4/2005 | Williamson |
| 2005/0107883 | A1 | 5/2005 | Goodfried et al. |
| 2005/0107884 | A1 | 5/2005 | Johnson et al. |
| 2005/0119664 | A1 | 6/2005 | Carignan et al. |
| 2005/0143745 | A1 | 6/2005 | Hodorek et al. |
| 2005/0148843 | A1 | 7/2005 | Roose |
| 2005/0171545 | A1 | 8/2005 | Walsh et al. |
| 2005/0171612 | A1 | 8/2005 | Rolston |
| 2005/0192588 | A1 | 9/2005 | Garcia |
| 2005/0216305 | A1 | 9/2005 | Funderud |
| 2005/0234461 | A1 | 10/2005 | Burdulis, Jr. et al. |
| 2005/0267584 | A1 | 12/2005 | Burdulis et al. |
| 2006/0052795 | A1 | 3/2006 | Burdulis et al. |
| 2006/0111722 | A1 | 5/2006 | Bouadi |
| 2006/0149283 | A1 | 7/2006 | May et al. |
| 2006/0200162 | A1 | 9/2006 | Farling et al. |
| 2006/0235421 | A1 | 10/2006 | Rosa et al. |
| 2007/0015995 | A1 | 1/2007 | Lang |
| 2007/0073305 | A1 | 3/2007 | Lionberger et al. |
| 2007/0118141 | A1 | 5/2007 | Marchyn et al. |
| 2007/0150065 | A1 | 6/2007 | Angibaud |
| 2007/0162025 | A1 | 7/2007 | Tornier et al. |
| 2007/0198022 | A1 | 8/2007 | Lang et al. |
| 2007/0203430 | A1 | 8/2007 | Lang et al. |
| 2007/0203455 | A1 | 8/2007 | Tremaglio et al. |
| 2007/0233128 | A1 | 10/2007 | Schmieding et al. |
| 2007/0233151 | A1 | 10/2007 | Chudik |
| 2007/0233156 | A1 | 10/2007 | Metzger |
| 2007/0276224 | A1 | 11/2007 | Lang et al. |
| 2007/0293868 | A1 | 12/2007 | Delfosse et al. |
| 2008/0004709 | A1 | 1/2008 | O'Neill et al. |
| 2008/0015433 | A1 | 1/2008 | Alexander et al. |
| 2008/0025463 | A1 | 1/2008 | Lang et al. |
| 2008/0031412 | A1 | 2/2008 | Delfosse et al. |
| 2008/0058613 | A1 | 3/2008 | Lang et al. |
| 2008/0058945 | A1 | 3/2008 | Hajaj et al. |
| 2008/0114370 | A1 | 5/2008 | Schoenefeld |
| 2008/0170659 | A1 | 7/2008 | Lang et al. |
| 2008/0195109 | A1 | 8/2008 | Hunter et al. |
| 2008/0195216 | A1 | 8/2008 | Lang |
| 2008/0219412 | A1 | 9/2008 | Lang |
| 2008/0243127 | A1 | 10/2008 | Lang |
| 2008/0255565 | A1 | 10/2008 | Fletcher |
| 2008/0275452 | A1 | 11/2008 | Lang et al. |
| 2008/0281328 | A1 | 11/2008 | Lang et al. |
| 2008/0281329 | A1 | 11/2008 | Lang et al. |
| 2008/0281426 | A1 | 11/2008 | Fitz et al. |
| 2008/0287953 | A1 | 11/2008 | Sers |
| 2009/0024131 | A1 | 1/2009 | Metzger et al. |
| 2009/0043310 | A1 | 2/2009 | Rasmussen |
| 2009/0054992 | A1 * | 2/2009 | Landes .............. A61B 17/1682 623/47 |
| 2009/0076371 | A1 | 3/2009 | Lang et al. |
| 2009/0087276 | A1 | 4/2009 | Rose |
| 2009/0088753 | A1 | 4/2009 | Aram et al. |
| 2009/0088758 | A1 | 4/2009 | Bennett |
| 2009/0099567 | A1 | 4/2009 | Zajac |
| 2009/0131941 | A1 | 5/2009 | Park et al. |
| 2009/0131942 | A1 | 5/2009 | Aker et al. |
| 2009/0149964 | A1 | 6/2009 | May et al. |
| 2009/0198244 | A1 | 8/2009 | Leibel |
| 2009/0204115 | A1 | 8/2009 | Dees et al. |
| 2009/0222014 | A1 | 9/2009 | Bojarski et al. |
| 2009/0307893 | A1 | 12/2009 | Bojarski et al. |
| 2010/0076441 | A1 | 3/2010 | May et al. |
| 2010/0160917 | A1 | 6/2010 | Fitz et al. |
| 2010/0240010 | A1 * | 9/2010 | Holmstrom .......... A61C 8/0025 433/173 |
| 2010/0262150 | A1 | 10/2010 | Lian |
| 2010/0274251 | A1 | 10/2010 | Ranft |
| 2010/0281678 | A1 | 11/2010 | Burdulis, Jr. et al. |
| 2010/0298894 | A1 | 11/2010 | Bojarski et al. |
| 2010/0305573 | A1 | 12/2010 | Fitz et al. |
| 2010/0305574 | A1 | 12/2010 | Fitz et al. |
| 2011/0066193 | A1 | 3/2011 | Lang et al. |
| 2011/0071581 | A1 | 3/2011 | Lang et al. |
| 2011/0213368 | A1 | 9/2011 | Fitz et al. |
| 2011/0213373 | A1 | 9/2011 | Fitz et al. |
| 2011/0213374 | A1 | 9/2011 | Fitz et al. |
| 2011/0213377 | A1 | 9/2011 | Lang et al. |
| 2011/0213427 | A1 | 9/2011 | Fitz et al. |
| 2011/0213428 | A1 | 9/2011 | Fitz et al. |
| 2011/0213429 | A1 | 9/2011 | Lang et al. |
| 2011/0213430 | A1 | 9/2011 | Lang et al. |
| 2011/0213431 | A1 | 9/2011 | Fitz et al. |
| 2011/0218539 | A1 | 9/2011 | Fitz et al. |

(56) References Cited

U.S. PATENT DOCUMENTS

| | | | | |
|---|---|---|---|---|
| 2011/0218542 | A1 | 9/2011 | Lian et al. | |
| 2011/0218584 | A1 | 9/2011 | Fitz et al. | |
| 2011/0230888 | A1 | 9/2011 | Lang et al. | |
| 2011/0238073 | A1 | 9/2011 | Lang et al. | |
| 2011/0313423 | A1 | 12/2011 | Lang et al. | |
| 2011/0319897 | A1 | 12/2011 | Lang et al. | |
| 2011/0319900 | A1 | 12/2011 | Lang et al. | |
| 2012/0029520 | A1 | 2/2012 | Lang et al. | |
| 2012/0041446 | A1 | 2/2012 | Wong et al. | |
| 2012/0065638 | A1* | 3/2012 | Moore | A61B 17/7225 606/62 |
| 2012/0066892 | A1 | 3/2012 | Lang et al. | |
| 2012/0071881 | A1 | 3/2012 | Lang et al. | |
| 2012/0071882 | A1 | 3/2012 | Lang et al. | |
| 2012/0071883 | A1 | 3/2012 | Lang et al. | |
| 2012/0072185 | A1 | 3/2012 | Lang et al. | |
| 2012/0101503 | A1 | 4/2012 | Lang et al. | |
| 2012/0143197 | A1 | 6/2012 | Lang et al. | |
| 2012/0151730 | A1 | 6/2012 | Fitz et al. | |
| 2012/0158001 | A1 | 6/2012 | Burdulis, Jr. et al. | |
| 2013/0261628 | A1 | 10/2013 | Burley et al. | |
| 2014/0180426 | A1* | 6/2014 | Lian | A61F 2/4606 623/20.15 |
| 2014/0270065 | A1 | 9/2014 | Aram et al. | |
| 2014/0275955 | A1 | 9/2014 | Crawford et al. | |
| 2014/0276853 | A1 | 9/2014 | Long et al. | |
| 2015/0320567 | A1 | 11/2015 | Terrill et al. | |
| 2016/0262903 | A1 | 9/2016 | West | |
| 2018/0055648 | A1* | 3/2018 | Dhillon | A61F 2/4202 |
| 2018/0303490 | A1 | 10/2018 | Loring et al. | |
| 2019/0070012 | A1 | 3/2019 | Leemrijse et al. | |
| 2019/0209080 | A1 | 7/2019 | Gullotti et al. | |
| 2020/0015867 | A1 | 1/2020 | Luna et al. | |
| 2020/0113712 | A1 | 4/2020 | Luna et al. | |
| 2020/0237519 | A1 | 7/2020 | Ball et al. | |
| 2020/0330238 | A1 | 10/2020 | Calamel et al. | |
| 2020/0337850 | A1 | 10/2020 | Reiley | |
| 2021/0378753 | A1 | 12/2021 | Christen et al. | |
| 2022/0280307 | A1 | 9/2022 | Haddad et al. | |
| 2022/0316504 | A1 | 10/2022 | Kubacki | |

FOREIGN PATENT DOCUMENTS

| | | |
|---|---|---|
| DE | 2306552 | 8/1974 |
| DE | 3516743 | 11/1986 |
| DE | 44 34 539 | 4/1996 |
| DE | 19501069 | 7/1996 |
| DE | 20303498 | 8/2003 |
| DE | 202008017199 | 3/2009 |
| DE | 202008017200 | 3/2009 |
| EP | 0377901 | 10/1989 |
| EP | 0528080 | 2/1993 |
| EP | 0530804 | 10/1993 |
| EP | 0626156 | 11/1994 |
| EP | 0704193 | 4/1996 |
| EP | 0896825 | 2/1999 |
| EP | 0938869 | 9/1999 |
| EP | 0613380 | 12/1999 |
| EP | 0993807 | 4/2000 |
| EP | 1074229 | 2/2001 |
| EP | 1077253 | 2/2001 |
| EP | 1120087 | 8/2001 |
| EP | 1129675 | 9/2001 |
| EP | 1132061 | 9/2001 |
| EP | 0732091 | 12/2001 |
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |
| EP | 1623686 A2 | 2/2006 |
| EP | 2124832 | 12/2009 |
| FR | 2819714 | 7/2002 |
| GB | 1451283 | 9/1976 |
| GB | 2291355 | 1/1996 |
| GB | 2348373 | 10/2000 |
| JP | 8-173465 | 7/1996 |
| JP | 9-206322 | 8/1997 |
| JP | 2000093435 | 4/2000 |
| JP | 2002-102236 | 4/2002 |
| JP | 2008-537689 | 9/2008 |
| JP | 2009515610 | 4/2009 |
| WO | WO 87/02882 | 5/1987 |
| WO | WO 90/009769 | 9/1990 |
| WO | WO 93/004710 | 3/1993 |
| WO | WO 93/009819 | 5/1993 |
| WO | WO 93/025157 | 12/1993 |
| WO | WO 95/027450 | 10/1995 |
| WO | WO 95/028688 | 10/1995 |
| WO | WO 95/030390 | 11/1995 |
| WO | WO 95/032623 | 12/1995 |
| WO | WO 96/024302 | 8/1996 |
| WO | WO 97/025942 | 7/1997 |
| WO | WO 97/026847 | 7/1997 |
| WO | WO 97/027885 | 8/1997 |
| WO | WO 97/038676 | 10/1997 |
| WO | WO 98/012994 | 4/1998 |
| WO | WO 98/20816 | 5/1998 |
| WO | WO 98/030617 | 7/1998 |
| WO | WO 98/32384 | 7/1998 |
| WO | WO 99/002654 | 1/1999 |
| WO | WO 99/008598 | 2/1999 |
| WO | WO 99/008728 | 2/1999 |
| WO | WO 99/042061 | 8/1999 |
| WO | WO 99/047186 | 9/1999 |
| WO | WO 99/051719 | 10/1999 |
| WO | WO 99/056674 | 11/1999 |
| WO | WO 00/009179 | 2/2000 |
| WO | WO 00/015153 | 3/2000 |
| WO | WO 00/035346 | 6/2000 |
| WO | WO 00/048550 | 8/2000 |
| WO | WO 00/059411 | 10/2000 |
| WO | WO 00/074554 | 12/2000 |
| WO | WO 01/010356 | 2/2001 |
| WO | WO 01/017463 | 3/2001 |
| WO | WO 01/019254 | 3/2001 |
| WO | WO 01/035968 | 5/2001 |
| WO | WO 01/045764 | 6/2001 |
| WO | WO 01/068800 | 9/2001 |
| WO | WO 01/070142 | 9/2001 |
| WO | WO 01/091672 | 12/2001 |
| WO | WO 02/000270 | 1/2002 |
| WO | WO 02/000275 | 1/2002 |
| WO | WO 02/002158 | 1/2002 |
| WO | WO 02/022013 | 3/2002 |
| WO | WO 02/022014 | 3/2002 |
| WO | WO 02/023483 | 3/2002 |
| WO | WO 02/034310 | 5/2002 |
| WO | WO 02/036147 | 5/2002 |
| WO | WO 02/096268 | 12/2002 |
| WO | WO 03/007788 | 1/2003 |
| WO | WO 03/037192 | 5/2003 |
| WO | WO 03/047470 | 6/2003 |
| WO | WO 03/051210 | 6/2003 |
| WO | WO 03/055400 | 7/2003 |
| WO | WO 2003/065907 | 8/2003 |
| WO | WO 04/043305 | 5/2004 |
| WO | WO 04/049981 | 6/2004 |
| WO | WO 05/051239 | 6/2005 |
| WO | WO 05/051240 | 6/2005 |
| WO | WO 06/060795 | 6/2006 |
| WO | WO 06/127283 | 11/2006 |
| WO | WO 07/041375 | 4/2007 |
| WO | WO 2007/061983 | 5/2007 |
| WO | WO 07/092841 | 8/2007 |
| WO | WO 08/112996 | 9/2008 |
| WO | WO 08/157412 | 12/2008 |
| WO | WO 2009/001083 | 12/2008 |
| WO | WO 09/111639 | 9/2009 |
| WO | WO2009143374 | 11/2009 |
| WO | WO2009158522 | 12/2009 |
| WO | WO 2010/099142 | 9/2010 |
| WO | WO 2010/120346 | 10/2010 |

(56) References Cited

FOREIGN PATENT DOCUMENTS

| | | |
|---|---|---|
| WO | WO 2010/121147 | 10/2010 |
| WO | WO2010135156 | 11/2010 |
| WO | WO 2011/110374 | 9/2011 |
| WO | WO2012121726 | 9/2012 |
| WO | WO2019009891 | 4/2019 |
| WO | WO2020124047 | 6/2020 |
| WO | WO 2020124052 | 6/2020 |
| WO | WO 2020242542 | 12/2020 |
| WO | WO 2022015877 | 1/2022 |
| WO | WO 2022094052 | 5/2022 |

OTHER PUBLICATIONS

Andersson, et al., "Macintosh Arthroplasty in Rheumatoid Arthritis," Acta. Orthrop. Scand., 1974, pp. 245-259, 45(2).
Anonymous: "Angle bracket (fastener)—Wikipedia", May 22, 2021, 1 page.
Anonymous: "Light Tube—Wikipedia", Mar. 4, 2021, 11 pages.
Anonymous: Newtonian Telescope—Wikipedia, May 23, 2021, 6 pages.
Argenson, et al., "Is There a Place for Patellofemoral Arthroplasty?," Clinical Orthopaedics and Related Research No. 321, 1995, pp. 162-167.
Birnbaum, et al., "Computer-Assisted Orthopedic Surgery with Individual Templates and Comparison to Conventional Operation Method," Spine, Feb. 2001, pp. 365-369, vol. 26, No. 4.
Chelule, et al., "Computer Aided Design of Personalized Jigs in Total Knee Replacement," 3rd Annual Meeting of CAOS Int'l Proc., Jun. 18-21, 2003, pp. 58-59, Spain.
Dare, S., Bobyn, J., Drouin, G., Dussault, R., Gariepy, R., "Use of Computerized Tomography and Numerical Control Machining for the Fabrication of Custom Arthroplasty Prostheses." Second World Congress on Biomaterials, 10th Annual Meeting of the Society for Biomaterials, p. 233, Washington, D.C., Apr. 27-May 1, 1984.
DePuy Synthes, "Flexible Reamers for Intramedullary Nails" Surgical Technique, 22 pages, 2017.
De Winter, et al., "The Richards Type II Patellofemoral Arthroplasty," Acta Orthop Scand, 2001, pp. 487-490, 72(5).
Delp, et al., "A Graphics-Based Software System to Develop and Analyze Models of Musculoskeletal Structures," Comput. Biol. Med., 1995, pp. 21-34, vol. 25, No. 1.
Farrar, et al., "Computed Tomography Scan Scout Film for Measurement of Femoral Axis in Knee Arthroplasty," J. Arthroplasty, 1999, pp. 1030-1031, vol. 14, No. 8.
Official Action for U.S. Appl. No. 13/465,547, dated Feb. 26, 2014.
First Office Action for Japanese Patent Appln. No. 2011-552091, dated Oct. 25, 2013.
Froemel, et al., "Computer Assisted Template Based Navigation for Total Knee Replacement," Documents presented at CAOS on Jun. 17, 2001, 4 pages.
Hafez, et al., "Computer Assisted Total Knee Replacement: Could a Two-Piece Custom Template Replace the Complex Conventional Instrumentations?", 4th Annual Meeting of CAOS Int'l Proc., Jun. 16-19, 2004, pp. 63-64, Chicago.
Hafez, et al., "Computer-Assisted Total Hip Arthroplasty: The Present and the Future," Future Rheumatol., 2006, pp. 121-131, vol. 1.
Kim, et al., "Measurement of Femoral Neck Anteversion in 3D. Part 1: 3D Imaging Method," Med. and Biol. Eng. and Computing, 2000, pp. 603-609, vol. 38, No. 6.
Lam, et al., "X-Ray Diagnosis: A Physician's Approach," 1998, Title page and Table of Contents pages Only, ISBN 9813083247, Springer-Verlag publishers.
Lam et al.. "VarusNalgus Alignment of the Femoral Component in Total Knee Arthroplasty," The Knee, 2003, pp. 237-241, vol. 10.
Lu, et al., "In Vitro Degradation of Porous poly(L-lactic acid) Foams," Biomaterials, Aug. 2000, pp. 1595-1605, 21(15).
Mahaisavariya, et al., "Morphological Study of the Proximal Femur: a New Method of Geometrical Assessment Using 3-Dimensional Reverse Engineering", Medical Engineering & Physics 24 (2002) pp. 617-622.
Marler, et al., "Soft-Tissue Augmentation with Injectable Alginate and Synegeneic Fibroblasts," Plastic & Reconstructive Surgery, May 2000 pp. 2049-2058, 105(6).
PCT/US2010/025143, International Preliminary Report on Patentability and Written Opinion, Sep. 9, 2011.
Portheine, et al., "Potentials of CT-based Planning and Template-based Procedure in Hip and Knee Surgery," Orth. Prac., 2000, pp. 786-791, vol. 36, English Translation with Certification.
Radermacher, "Computer Assisted Matching of Planning and Execution in Orthopedic Surgery," Slide Presentation, Nov. 29, 1993, 22 pages.
Radermacher, "Template Based Navigation—An Efficient Technique for Hip and Knee Surgery," CAOS First Asian Meet, Mar. 27-28, 2004, pp. 45-50, India.
Radermacher, et al., "Computer-Assisted Planning and Operation in Orthopedics," Orth. Prac. 36th Year, Dec. 2000, pp. 731-737, English Translation with Certification.
Rau, et al., "Small and Neat," Medical Tech. Int'l, 1993-94, pp. 65, 67 and 69.
Schkommadau, et al., "Clinical Experience With the Individual Template Technique," Orth. Prac., 2001, pp. 19-22, vol. 37, No. 1, English Translation with Certification.
Seel, et al., "Three-Dimensional Planning and Virtual Radiographs in Revision Total Hip Arthroplasty for Instability," Clinical Orthopaedics and Related Research, Jan. 2006, pp. 35-38, No. 442.
Slone, et al., "Body CT: A Practical Approach," 1999, Title page and Table of Contents pages Only, ISBN 007058219, McGraw-Hill.
Staudte, et al., "Computer-Assisted Operation Planning and Technique in Orthopedics," North Rhine-Westphalia Acad. for Sciences, Lecture N.444, 2000, 17 pages, ISSN 0944-8799, in German.
Staudte, et al., "Computer-Assisted Operation Planning and Technique in Orthopedics," North Rhine-Westphalia Acad. for Sciences, Lecture N.444, 2000, 34 pages, ISSN 0944-8799, English Translation with Certification.
Stauffer, et al., "The Macintosh Prosthesis. Prospective Clinical and Gait Evaluation," Arch. Surg., 1975, pp. 717-720, 110(6).
Stout, et al., "X-Ray Structure Determination: A Practical Guide," 1989, Title page and Table of Contents pages Only, ISBN 0471607118, John Wiley & Sons.
Stryker Trauma GmbH, "Bixcut Reamer System" Osteosynthesis, 8 sheets, 2009.
Synthes, "SynReam, The Synthes Reaming System" Surgical Technique, 22 pages, 2005.
Tamez-Pena, et al., "MRIIsotropic Resolution Reconstruction from Two Orthogonal Scans," Proceedings of the SPIE—The International Society for Optical Engineering SOIE-OMT, 2001, pp. 87-97, vol. 4322.
Testi, et al., "Border Tracing Algorithm Implementation for the Femoral Geometry Reconstruction," Camp. Meth. and Programs in Biomed., 2001, pp. 175-182, vol. 65.
Vandeberg, et al., "Assessment of Knee Cartilage in Cadavers with Dual-Detector Spiral CT Arthrography and MR Imaging," Radiology, Feb. 2002, pp. 430-435, 222(2).
Wiese, et al., "Biomaterial Properties and Biocompatibility in Cell Culture of a Novel Self-Inflating Hydrogel Tissue Expander," J. Biomedical Materials Research Part A, Nov. 2000, pp. 179-188, 54(2).
Woolson, S., Fellingham, L., Dev, P., and Vassiliadis, A., "Three Dimensional Imaging of Bone from Analysis of Computed Tomography Data." Orthopedics, vol. 8, No. 10, pp. 1269-1273, Oct. 1985.
Yusof, et al., "Preparation and Characterization of Chitin Beads as a Wound Dressing Precursor," J. Biomedical Materials Research Part A, Oct. 2000, pp. 59-68, 54(1).
Examination Report issued in connection with corresponding Indian Patent Application No. 2004/KOLNP/2013, Nov. 27, 2018, 7 pages.
First Office Action issued in connection with corresponding Chinese Patent Application No. 201610973637.8, Nov. 28, 2018, 6 pages.

(56) References Cited

OTHER PUBLICATIONS

First Examination Repot issued in connection with corresponding Australian Patent Application No. 2018204063, Jul. 10, 2019, 2 pages.
Second Examination Report issued in connection with corresponding Australian Patent Application No. 2019261830, May 4, 2021, 9 pages.
First Examination Repot issued in connection with corresponding Australian Patent Application No. 201926183, Dec. 21, 2020, 4 pages.
International Search Report and Written Opinion issued in connection with International Patent Application No. PCT/US2022/070130, May 13, 2022, 17 pages.
Extended European Search Report issued in connection with European Patent Application No. 22172072, May 4, 2023, 25 pages.

* cited by examiner

IMPLANTS WITH MODULAR STEMS WITH TENSION/COMPRESSION MECHANISMS

CROSS-REFERENCE TO RELATED APPLICATION

This application claims priority under 35 U.S.C. § 119(e) to U.S. Provisional Application No. 63/377,423, filed Sep. 28, 2022, the entirety of which is incorporated herein by reference.

INCORPORATION BY REFERENCE

The present application incorporates by reference the entire disclosures of U.S. patent application Ser. No. 17/649,088, filed Jan. 27, 2022; U.S. Patent Application No. 63/156,452, filed Mar. 4, 2021; U.S. Patent Application No. 63/193,280, filed May 26, 2021; and U.S. Patent Application No. 63/374,248, filed Sep. 1, 2022, entitled "Multiaxial Modular Stems."

FIELD

The present disclosure is related to modular implants. More specifically, the disclosed systems and methods relate to modular stems and implants, including stems and implants that may be used in a total ankle replacement.

BACKGROUND

Tibia stem components help engage implants where limited bone is available for total ankle arthroplasty. Pistoning or loosening of the implant can present as a long-term complication. Thus, improved tibia stem components that can better engage with the tibia and improve immediate implant stability and reduce implant migration over time are desired.

SUMMARY

Disclosed herein are implants designed to engage cancellous, and possibly cortical, tibia bone to improve immediate implant stability and reduce implant migration over long term. Although the implants are described as being used in connection with a total ankle replacement, it should be understood that the modular stems and connection techniques described herein may be used with other joints, including the knee, shoulder, and hips, for example.

In some aspects, a prosthesis includes a first component, a second component, and a coupling member. The first component may include a first body extending from a first end to a second end. The second end of the first component may define a first opening that extends inwardly toward the first end of the first component. The first opening may include a first portion having a first diameter and a second portion having a second diameter that is different from the first diameter. The second component may include a second body extending from a first end to a second end. The second body may define a second opening that extends through the second body from the first end of the second body to the second end of the second body. The coupling member may be configured to couple the first component and the second component by compressing the first component and the second component. The coupling member may include a shaft portion and a head portion. The shaft portion may be sized and configured to be received in the first opening and the second opening.

In some aspects, the second body of the second component may include a protrusion extending from a shoulder. The protrusion may be sized and configured to be at least partially received in the first portion of the first opening defined by the first component.

In some aspects, each of the first portion of the first opening and the protrusion of the second body may include a respective taper. The respective tapers may be configured to engage one another.

In some aspects, the second portion of the first opening may include at least one first thread. The shaft of the coupling member may include at least one second thread. The at least one second thread may be configured to engage the at least one first thread.

In some aspects, the second opening defined by the second component may include a first portion, a second portion, and a third portion. The first portion may include a taper. The second portion may be sized and configured to at least partially receive the head of the coupling member. The third portion may have a diameter that is greater than a diameter of the shaft of the coupling member and smaller than a diameter of the head portion of the coupling member.

In some aspects, the first opening may include a third portion. The second portion of the first opening may be located between the first portion of the first opening and the third portion of the first opening. The first opening may be sized and configured to receive the head portion of the coupling member.

In some aspects, the coupling member may include a tensioning wire comprising the head portion and the shaft portion. A collet may define a third opening and may include a plurality of flexible arms. The third opening may be sized and configured to receive the shaft portion of the tensioning wire.

In some aspects, the second opening defined by the second component may include a first portion and a second portion. The first portion of the second opening may include at least one thread sized and configured to be engaged by a thread disposed on an outer surface of the collet. The second portion may include taper configured to engage the plurality of flexible arms.

In some aspects, the first portion of the second opening may include a taper sized and configured to engage a protrusion of another component.

In some aspects, a third component may have a third body. The third body may include a pair of spaced apart rails and a protrusion extending from an upper surface of the third body. The protrusion may be sized and configured to be received in at least one of the first opening or the second opening.

In some aspects, the third body may define a fourth opening sized and configured to receive the collet therein. The fourth opening defined by the third body may include a first portion and a second portion. The first portion may include at least one thread configured to engage at least one thread disposed on an outer surface of the collet. The second portion may include a taper configured to engage the plurality of flexible arms.

In some aspects, the first portion may include at least one anti-rotation feature extending from and outer surface. The at least one anti-rotation feature may include a plurality of fins extending from the first end of the first body toward the second end of the first body.

In some aspects, the first portion may include surface texturing to promote bone ingrowth/ongrowth. The surface texturing may include at least one groove formed in an outer surface of the first body. The at least one groove may include at least one circumferential groove. The at least one groove may include at least one helical groove.

In some aspects, the surface texturing may include a texture formed by grit blasting.

In some aspects, the first body may include an elongate cylindrical section disposed between the first end of the first body and the second end of the first body.

In some aspects, a method is provided. The method may include inserting a first component of a prosthesis into a resected joint space disposed between a first bone and a second bone. The first component may be advanced into an intramedullary canal formed in the first bone. A second component of the prosthesis may be inserted into the resected joint space. A coupling component may be inserted into a first opening defined by the first component and into a second opening defined by the second component. The coupling component may be rotated to compress the first component and the second component.

In some aspects, the coupling component may include at least one thread that engages at least one thread disposed within the first opening defined by the first component.

In some aspects, a method may include aligning a protrusion of the second component with the first opening defined by the first component such that the protrusion may be received in the opening defined by the first component.

In some aspects, a method may include inserting a third component into the resected joint space. Rotating the coupling component may include rotating the coupling component until at least a portion of a head portion of the coupling component is received in an opening defined by the third component.

In some aspects, the first bone may be a tibia and the second bone may be a talus.

In some aspects, a method may include inserting the coupling component into the resected joint space between the tibia and the talus through an intramedullary canal formed in the talus and a calcaneus.

In some aspects, a method may include inserting the coupling component into the resected joint space between the tibia and the talus.

In some aspects, a method may include inserting a first component of a prosthesis into a resected joint space disposed between a first bone a second bone. The first component of the prosthesis may include a flexible shaft portion of a tensioning wire extending from a trailing end. The first component may be advanced into an intramedullary canal formed in the first bone, and a second component of the prosthesis may be inserted into the resected joint space such that at least a portion of the flexible shaft portion of the tensioning wire is received in an opening defined by the second component. The tensioning wire may be tensioned to compress the first component and the second component.

In some aspects, a method may include inserting the trailing end of the flexible shaft portion into an opening defined by the first component such that the flexible shaft portion extends through the first component and a head portion of the tensioning wire is received within the opening defined by the first component.

In some aspects, a method may include snipping an excess portion of the flexible shaft portion of the tensioning wire.

In some aspects, a method may include inserting a third component of the prosthesis into the resected joint space such that at least a portion of the flexible shaft portion of the tensioning wire is received in an opening defined by the third component. Tensioning the tensioning wire to compress the first component and the second component may include compressing the first component, second component, and third component.

In some aspects, a method may include inserting the trailing end of the flexible shaft portion into an opening defined by a collet and coupling the collet to the third component of the prosthesis.

In some aspects, a method may include inserting a third component of the prosthesis into the resected joint space such that at least a portion of the flexible shaft portion of the tensioning wire is received in an opening defined by the third component and inserting a tibia tray component into the resected joint space such that a least a portion of the flexible shaft portion of the tensioning wire is received in and through an opening defined by a protrusion extending from an upper surface of the tibia tray component. A collet may be coupled to the tibia tray component.

In some aspects, tensioning the tensioning wire to compress the first component and the second component may include compressing the first component, second component, third component, and the tibia tray component.

In some aspects, coupling the collet to the tibia tray component may include inserting the collet into the opening defined by the protrusion of the tibia tray component.

BRIEF DESCRIPTION OF DRAWINGS

The features of the embodiments described herein will be more fully disclosed in the following detailed description, which is to be considered together with the accompanying drawings wherein like numbers refer to like parts. All drawings are schematic and are not intended to show actual dimensions or proportions.

DETAILED DESCRIPTION

Figure 1:
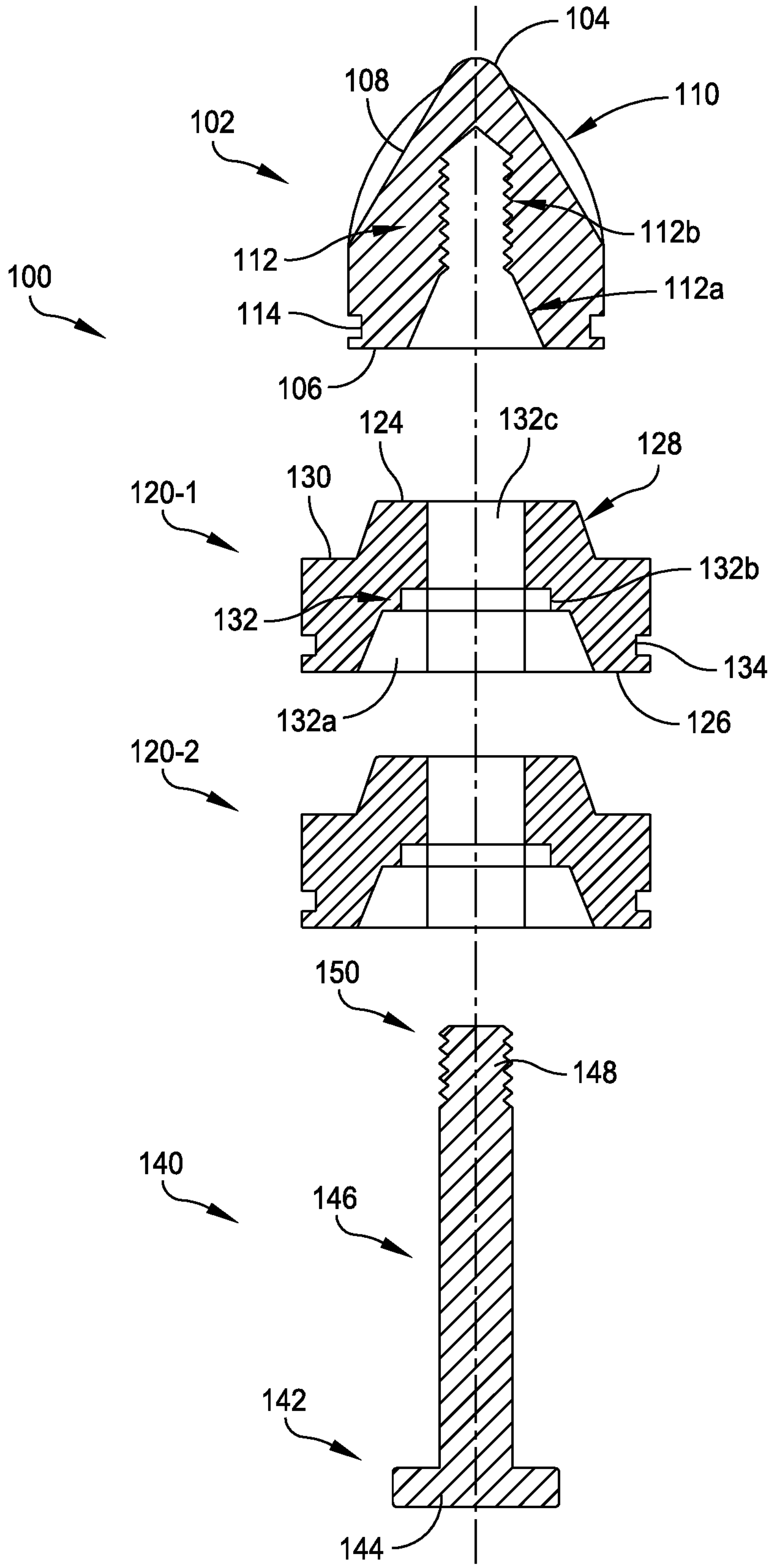
FIG. 1 illustrates one example of a prosthesis stem in accordance with some embodiments.

This description of the exemplary embodiments is to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

The methods, systems, and structures described for the ankle herein may be adapted to other applications in arthroplasty, including but not limited to the knee, shoulder, hip, elbow, and other joints.

FIG. 1 illustrates one example of a multi-component prosthesis stem in accordance with some embodiments. The stem 100 may be component of a larger prosthesis, such as a total ankle replacement system, although the stem 100 may be a standalone prosthesis. The stem shown in FIG. 1 may include a first component 102, one or more second components 120, and a coupling member 140. In the example illustrated in FIG. 1 two components 120-1, 120-2 are provided, although it should be understood that other combinations of components may be provided. For example, fewer (e.g., one) or more components 120 may be provided. Further, depending on the configuration of the first component 102, additional components 102 may be provided in a prosthesis.

The component 102, which may be referred to as a top or leading component, may extend in a longitudinal direction from a first end 104 to a second end 106. The leading component 102 may include a curved outer surface 108 that tapers as it extends from the second end 106 toward the first end 104. In some embodiments, one or more fins or counter-torque/anti-rotation features 110 may extend from the outer surface 108. The fins 110 may extend in a longitudinal direction, although the fins 110 may be disposed in other directions (e.g., helical, radial/circumferential, and combinations thereof). In some embodiments, the fins 110 may be interrupted such that each fin may include a plurality of fin segments as will be understood by one of ordinary skill in the art. Further, the counter-torque/anti-rotation features 110 may be deployable in response to the advancement of the coupling member 140, such as the retractable members radially expanding in response to a linear actuator as disclosed in U.S. Provisional Application No. 63/374,248, filed Sep. 1, 2022, which is incorporated by reference in its entirety.

The second end 106 may define an opening 112 that extends inwardly towards first end 104. Opening 112 may include a first portion 112*a* and a second portion 112*b*. The first portion 112*a* may taper from a first diameter to a second diameter in which the second diameter is smaller than the first diameter. The first portion 112*a* may be tapered to form a Morse taper, although first portion 112*a* may be otherwise tapered. For example, instead of being conical, the first portion 112*a* may be pyramidal and have a triangular or square shape such that the first portion 112*a* may provide a counter-torque or anti-rotation feature. In some embodiments, the second portion 112*b* may be threaded. An external engagement feature 114 may be disposed adjacent to the second end 106. The engagement element 114 may take a variety of forms, including one or more flats to facilitate engagement by a tool, such as a wrench. Other examples of engagement elements are disclosed in U.S. patent application Ser. No. 17/650,116, filed Feb. 2, 2022, the entirety of which is incorporated by reference herein.

Figure 2:
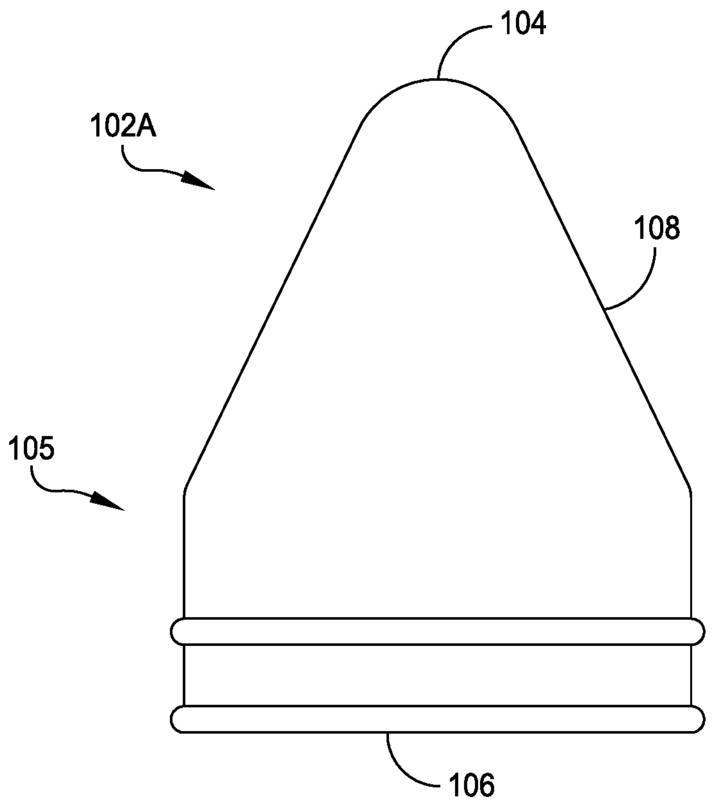
FIG. 2 illustrates one example of a component of a prosthesis stem in accordance with some embodiments.

In some embodiments, the external engagement feature 114 may be omitted. Further, in some embodiments, the top component may include a cylindrical portion 105 disposed between the first end 104 and the second end 106, as does the top component 102A shown in FIG. 2. The extended cylindrical portion may increase a length of the top stem component 102A compared to other top stem components, such as top stem component 102 shown in FIG. 2.

Figure 3A:
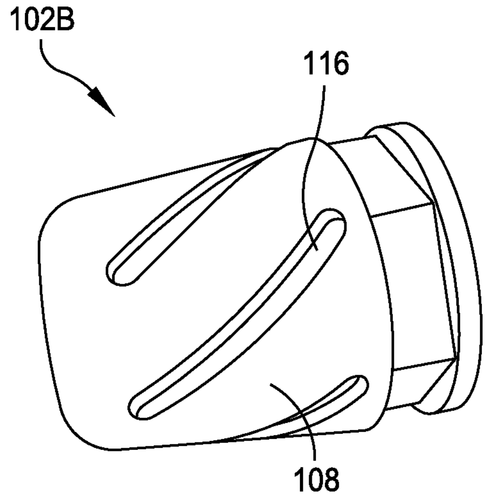
FIGS. 3A-3D illustrate examples of surface texturing that may be applied to prosthesis stem components in accordance with some embodiments.

Outer surface 108 may include one or more regions of plasma spray to promote bony ingrowth. However, in some embodiments, the outer surface may not include any plasma spray, but may include other texturing and/or features to promote ingrowth/ongrowth. For example, FIGS. 3A and 3B respectively illustrate examples of top components 102B, 1002C, which may include surface texturing. Referring first to the example illustrated in FIG. 3A, the top component 102B includes a plurality of discrete helical grooves 116 formed in the outer surface 108.

Figure 3B:
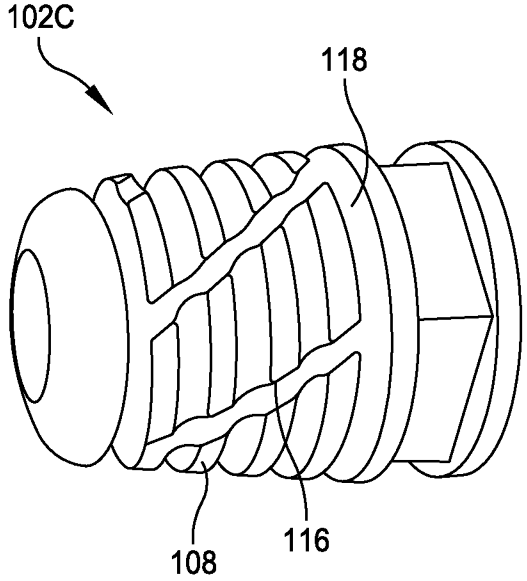

The top component 102C shown in FIG. 3B may include a plurality of helical grooves 116 and a plurality of radial/circumferential grooves 118 that may intersect the helical grooves 116. Forming grooves 116, 118 in the outer surface 108 of the top components 102B, 102C advantageously provides space to allow for ingrowth/ongrowth, which may be easier release compared to the ingrowth/ongrowth experienced by a plasma spray. Although not shown, it should be understood that a top component 102 may be provided with only radial/circumferential grooves and that other shapes and orientations of grooves (e.g., longitudinally oriented) may be provided. The outer surface 108 may also be grit blasted, which may be more economical and/or may provide for an implant that has tighter tolerance compared to a plasma sprayed implant.

Referring again to FIG. 1, component 120 may be a middle and/or trailing component that may be configured to be coupled to the top component 102. Component 120 may have a body 122 having a generally cylindrical shape and extend in a longitudinal direction from a first end 124 to a second end 126. In some embodiments, the length of the component 120 (e.g., a distance from the first end 124 to the second end 126) may be greater than a width (e.g., a diameter) of the component 120. However, it should be understood that length of the component 120 may be less than a width. In some embodiments, a kit may be provided in which a plurality of components 120 of differing sizes are provided in the kit.

Figure 3C:
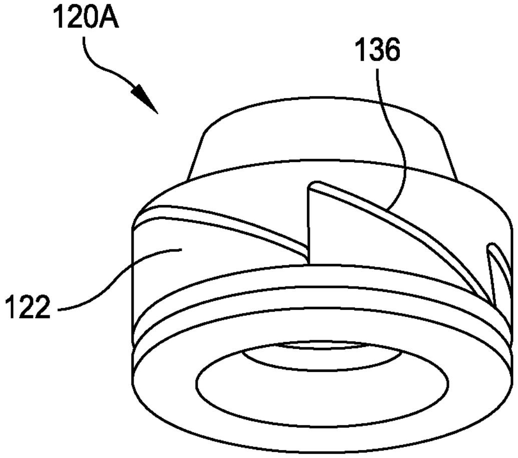
Figure 3D:
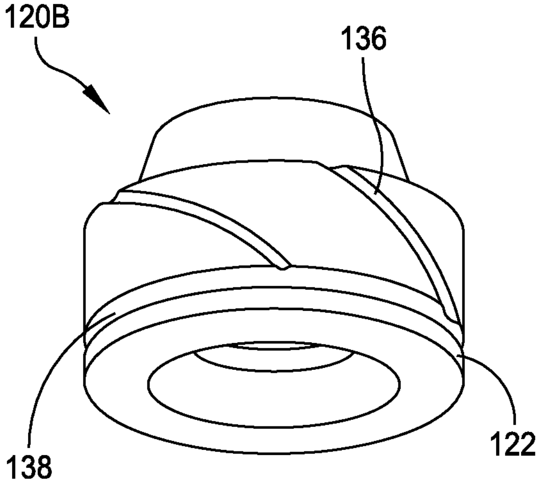
Figure 3E:
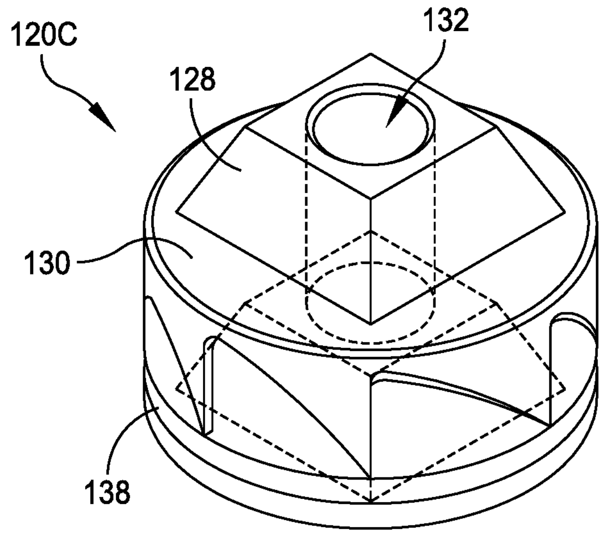
FIGS. 3E and 3F illustrate examples of stem components having differently shaped tapered regions or protrusions, in accordance with some embodiments.
Figure 3F:
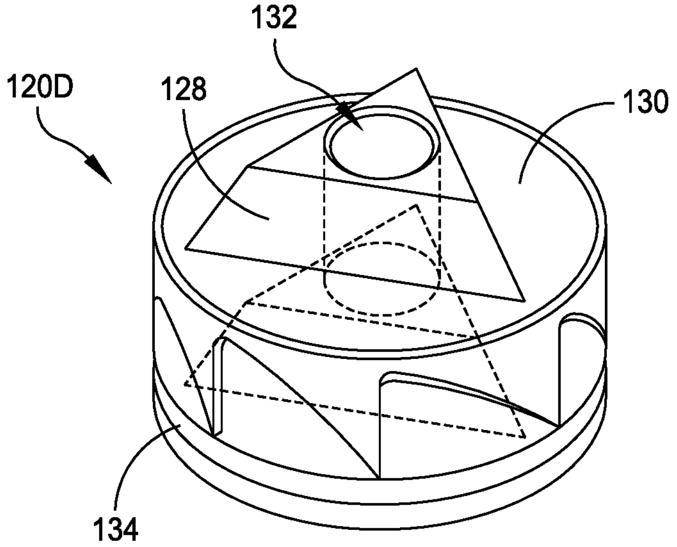

The first end 124 of the component 120 may include a tapered region 128, which may also be referred to as a coupling region, sized and configured to be received in at least a portion of the first portion 112*a* of the opening 112 of the top component 102. In some embodiments, the tapered region 128 extends from a shoulder 130 of the body 122. The tapered region 128 may be conical (as shown in FIGS. 3C and 3D), pyramidal (as shown in FIGS. 3E and 3F), or may have another shape that facilitates coupling of the component 120 to component 102 as will be understood by one of ordinary skill in the art.

The second end 126 of the component 120 may define an opening 132 that extends inwardly towards first end 124. In some embodiments, the opening 132 may extend entirely through body 122. Opening 132 may include a first portion 132*a*, a second portion 132*b*, and a third portion 132*c* that are in communication with one another. The first portion 132*a* may taper from a first diameter or width to a second diameter or width. The second diameter or width may be smaller than the first diameter or width. In some embodiments, the first portion 132*a* of the opening 132 may be configured to form a Morse tapered connection with another component, such as another component 120 and/or a tibia tray component, such as the tibia tray component 180 shown in FIG. 1. However, the first portion 132*a* may have other shapes, which may be complementary to the shapes of the protrusions of other components (e.g., a triangular or square pyramid, to list only a few possibilities). The second portion 132*b* may have a generally cylindrical shape with a third diameter, which may be smaller than the first diameter or width and the second diameter or width. The second portion 132*b* may be sized and configured to receive a portion of a coupling member, such as the head 144 of coupling member 140. The third portion 132*c* may also have a generally cylindrical shape and may have a fourth diameter. The fourth diameter may be smaller than the first diameter or width, second diameter or width, and third diameter. In some embodiments, the fourth diameter is sized to provide clearance to receive at least a portion of a coupling member, such as the shaft 146 of the coupling member 140.

An external engagement feature 134 may be disposed adjacent to the second end 126. The external engagement feature 134 may have a similar configuration (e.g., size and shape) to the engagement element 114 of the first component 102 such that the same tool may be used to engagement element 114 and engagement element 134. Accordingly, in some embodiments, the engagement element 134 may include one or more flats to facilitate engagement by a tool, such as a wrench. However, the engagement element may take a variety of forms, including the forms of the engagement elements disclosed in U.S. patent application Ser. No. 17/650,116. In some embodiments, the component 120 may be provided without an external engagement element 134.

The outer surface of the body 122 of component 120 may include surface texturing to promote ingrowth/ongrowth. For example, FIGS. 3C and 3D illustrate stem components 120A, 120B that includes surface texturing. Referring first to the example illustrated in FIG. 3C, the component 120A includes a plurality of discrete helical grooves 136 formed in the body 122. The component 102B shown in FIG. 3D may include a plurality of helical grooves 136 and a plurality of radial/circumferential grooves 138 that may intersect the helical grooves 136. Forming grooves 136, 138 in the body 122 of the components 120A, 120B advantageously provides space to allow for ingrowth/ongrowth, which may be easier release compared to the ingrowth/ongrowth experienced by a plasma spray. Although not shown, it should be understood that a component 120 may be provided with only radial/circumferential grooves and that other shapes and orientations of grooves (e.g., longitudinally oriented) may be provided. The body 122 may also be grit blasted, which may be more economical and/or may provide for an implant that has tighter tolerance compared to a plasma sprayed implant. In some embodiments, the body 122 may include a plurality of longitudinal fins that extend outwardly from the body 122. In some embodiments, the fins may be arranged in other orientations, such as helical or circumferential.

Coupling member 140 may be configured to couple the various components (e.g., the first component 102 and one or more second components 120) of the stem. Coupling member may also be configured to apply a tension to or across one or more of the components 102, 120 and/or be configured as a linear actuator as disclosed in U.S. Provisional Patent Application No. 63/374,248, as will be appreciated by one of ordinary skill in the art. In the example illustrated in FIG. 1, the coupling member 140 may include a head portion 142 and a shaft portion 146. The head portion 142 may have a generally cylindrical shape having a fifth diameter. The fifth diameter may be smaller than the first and second diameters or widths, but may be larger than the third and fourth diameters such that the head portion 142 may be received within the second portion 132*b* of the opening 132 defined by the second component 120. The head portion 142 may define an engagement feature 144, which may be sized and configured to be engaged by a tool. For example, the engagement feature 144 may include one or more slots or recesses configured to be engaged by a driving tool, such as an Allen wrench/key, a straight screwdriver, a Phillips-head screwdriver), or a Star/Torx driver, to list only a few possibilities.

The shaft portion 146 may extend from the head portion 142 and have a generally cylindrical shape with a sixth diameter. The sixth diameter may be the smallest diameter such that the shaft portion 146 may be received through the one or more second components 120 and at least be partially received within the opening 112. In some embodiments, the shaft portion 146 includes one or more threads 148 disposed at (e.g., adjacent to) the leading end 150. The one or more threads 148 may be configured to engage the threads of the second portion 112*b* of the first component 102. The one or more threads 148 may include anti-releasing features, such as Loctite, Spiralock, locking washer, or other thread locking features to reduce the chance of thread loosening. Coupling members 140 may be provided in a number of sizes (e.g., lengths and/or diameters) such that stems of various lengths may be formed from multiple stem components. For example, a kit may include a coupling member 140 having a first length that is configured to couple together a first component 102 and a single second component 120. The kit may also include a coupling member 140 having a second length that is configured to couple together a first component 102 and two second components 120. One of ordinary skill in the art will understand that other lengths may be provided. Providing coupling components 140 of differing lengths may provide a surgeon with flexibility to construct a stem of an appropriate length intraoperatively based upon the patient's anatomy.

In use, the patient's anatomy may be prepared, such as by reaming an intramedullary canal in bone, such as is described in U.S. Pat. No. 7,534,246, which is incorporated herein by reference in its entirety. The first component 102 may be inserted into the intramedullary canal. In some embodiments, the first component 102 may be inserted into the intramedullary canal by inserting the first component 102 into a resected joint space formed between a tibia and a talus such that the first component enters the joint space in an anterior-to-posterior direction. The first component 102 may be engaged by a tool and pressed into the intramedullary canal.

A second component (e.g., second component 120-1) may then be coupled to the first component 102 in situ by inserting the second component 120-1 into the resected joint space in an anterior-to-posterior direction. The second component 120-1 may be pressed into engagement with the first component 102 by aligning the two components and inserting the tapered region 128 of the second component 120-1 into the first portion 112*a* of the opening defined by the first component 102. The construct of the first component 102 and the second component 120-1 may be advanced farther into the intramedullary canal.

A third component, which may be component 120-2, may be coupled to the construct of the first component 102 and second component 120-1 by inserting the third component 120-2 into the resected joint space in an anterior-to-posterior direction. The third component 120-2 may be pressed into engagement with the construct of the first component 102 and the second component 120-1 by inserting the tapered region 128 of the third component 120-2 with the first portion 132*a* of the opening 132 of the second component 120-1.

When a stem of a desired length has been achieved, the components may be secured to one another through the use of a coupling member 140. For example, the shaft portion 146 of the coupling member 140 may be inserted into the first portion 132*a* of the opening of the third component 120-2. Depending on the length of the coupling member 140, it may be inserted through the anterior opening or it may be inserted through a path formed in a patient's calcaneus and talus. The coupling member 140 may be advanced axially such that the shaft portion extends through the third component 120-2 and the second component 120-1 (via openings 132) and is received in the opening 112 defined by the first component 102. The threads 148 of the coupling member 148 may engage the threaded portion 112*b* of the opening 112 defined by the first component 102. The coupling member 140 may be rotated to engage the threads 148 of the coupling member 140 and the first component 102 further. The anti-rotation features 110, which may be embedded within the surrounding bone, may resist rotation of the first component 102 as the coupling member 140 is rotated. In some embodiments, a tool may be used to engage the external engagement feature 134 of the second and/or third components 120-1, 120-2 as the coupling member is rotated to prevent these components from rotating.

The rotation of the coupling member 140 results in linear translation of the coupling member with respect to the first, second, and third components 102, 120-1, 120-2 resulting in the tensioning/compression of the stem components. The tensioning/compression also results in the corresponding tapered surfaces engaging one another and locking the stem components to one another. The stem shown in FIG. 1 may be assembled without the need to thread the individual components together, as required by some conventional multi-component designs. Providing stem components in the absence of threads may reduce the amount of work required to couple together the stem components in situ and may reduce the operating time.

Figure 4:
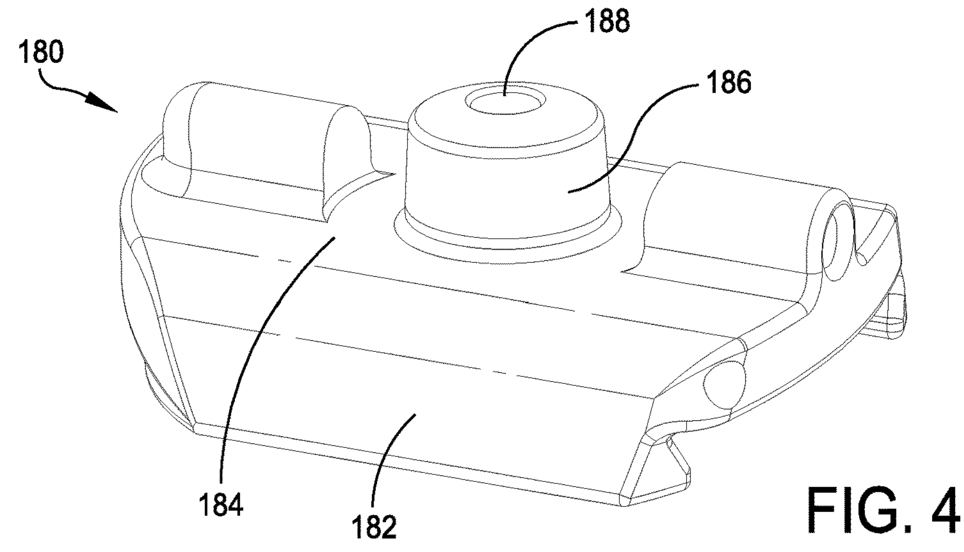
FIG. 4 illustrates one example of a tibia tray component that may be used with a stem prosthesis in accordance with some embodiments.
Figure 4A:
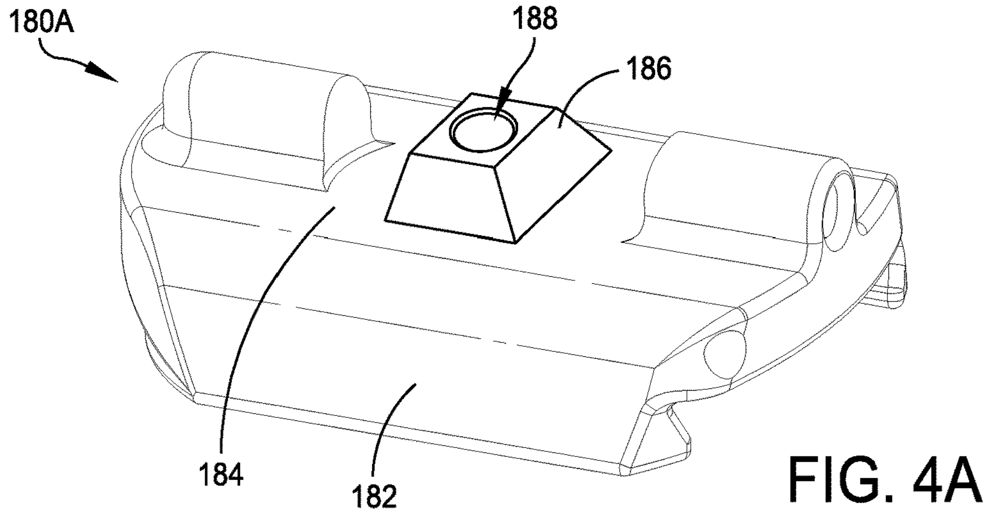
FIGS. 4A and 4B illustrate examples of tibia tray components having differently shaped tapered regions or protrusions, in accordance with some embodiments.
Figure 4B:
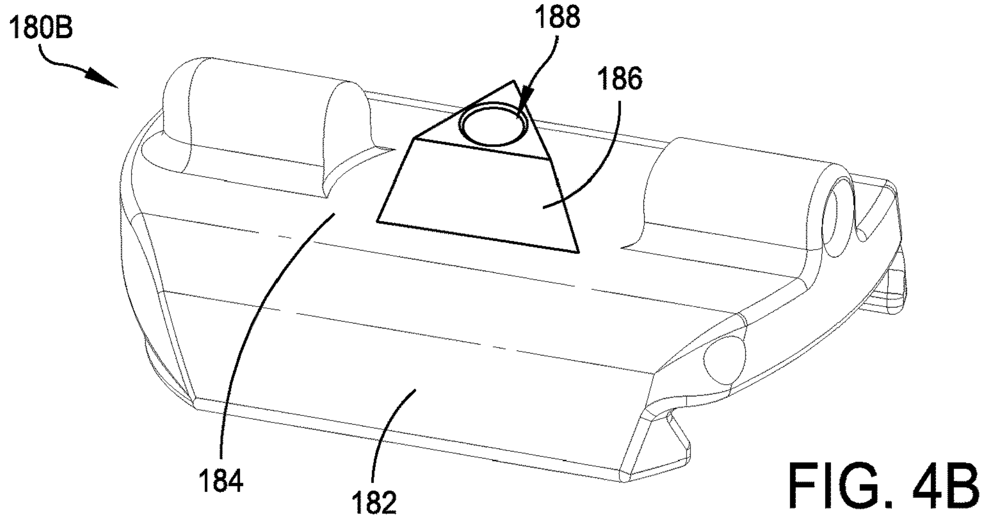

The stem 100 may be coupled to another component of a prosthesis in situ. For example, a tibia tray component, such as the tibia tray component 180 shown in FIG. 4, the tibia tray component 180A shown in FIG. 4A, and the tibia tray component 180B shown in FIG. 4B, may be coupled to the stem 100. For example, a tibia tray component 180, 180A, 180B may be inserted into the resection joint space between the tibia and the talus such that the protrusion 186 extending from an upper surface 184 of the body 182 aligns with the first portion 132*a* of the opening 132 defined by the third prosthesis component 120-2. As shown in FIGS. 4-4B, the protrusion 186 may be conical (FIG. 4), a square pyramid (FIG. 4A), a triangular pyramid (FIG. 4B), or have other shapes as will be understood by one of ordinary skill in the art. Because the head portion 144 of the coupling member 140 may be received entirely within the second portion 132*b* of the opening defined by the third prosthesis component 120-2, the all or at least a sufficient portion of the protrusion 186 may be received within the first portion 132*a* of the opening 132 defined by the third component 120-2. The protrusion 186 may be tapered such that the combination of the protrusion 186 and the first portion 132*a* of the opening of the third component 120-2 form a tapered connection.

It should be understood that other structures that are suitable for coupling the stem 100 and the tibia tray component 180 may be implemented. For example, the protrusion 186 may define an opening 188 that is sized and configured to receive a coupling member, such as a bolt, screw, or other fastener. The coupling member may be inserted into a corresponding recess defined in the head portion 144 of the coupling member 140 (not shown). One of ordinary skill in the art will understand that other methods of securing the tibia tray component 180 to the stem 100 may be used.

FIGS. 5-9 illustrate an example of a prosthesis in accordance with some embodiments. The prosthesis may include a stem 200 and a tibia tray component 280. The stem 200 may include a first component 202, one or more second components 220, a third component 220A, and a coupling member 240. In the example illustrated in FIGS. 5-9, one component 220 is provided, but it should be understood that other combinations of components may be provided. For example, more components 220 may be provided. Further, depending on the configuration of the first component 202, additional components 202 and/or components 220A may be provided in a prosthesis.

The component 202, which may be referred to as a top or leading component, may extend in a longitudinal direction from a first end 204 to a second end 206. The leading component 202 may include a curved outer surface 208 that tapers as it extends from the second end 206 toward the first end 204. Although not shown, anti-rotation/counter torque features, such as fins, may extend outwardly along the length of the top component 202. Additionally or alternatively, the top component 202 may include surface texturing, such as grooves, plasma spray, grit blasting, and/or other texturing to facilitate bone ingrowth/ongrowth.

Figure 9:
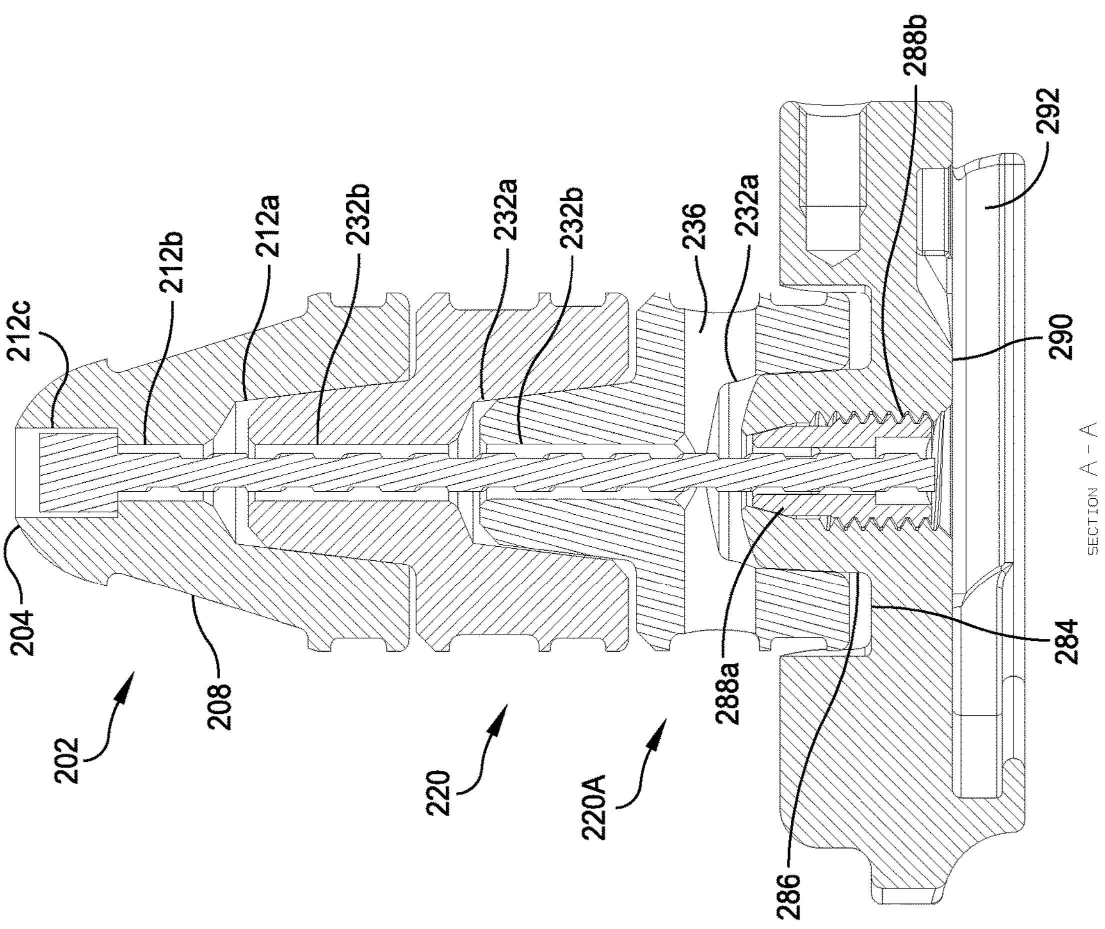
FIG. 9 is a cross-sectional view taken along line A-A in FIG. 8 in accordance with some embodiments.
Figure 8:
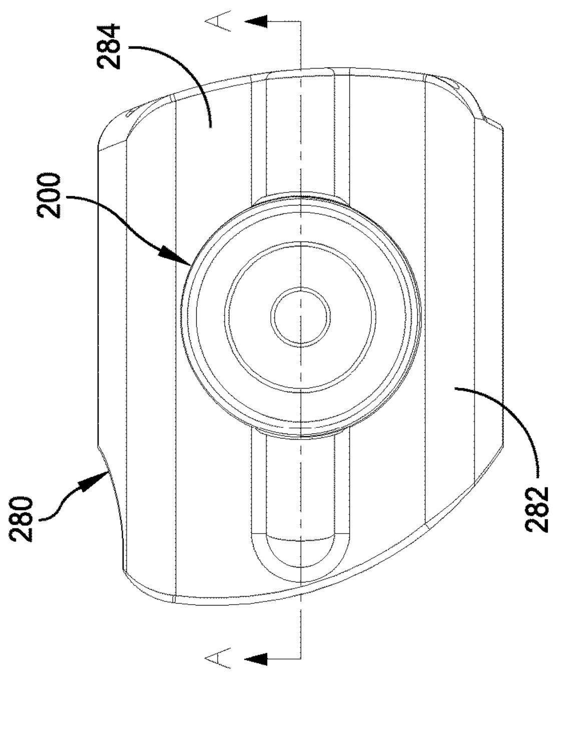
FIG. 8 is a top side view of the assembled prosthesis illustrated in FIG. 5 in accordance with some embodiments.

As best seen in FIG. 9, component 202 may define an opening 212 that extends from the first end 204 to the second end 206. Opening 212 may include a first portion 212*a*, a second portion 212*b*, and a third portion 212*c* that are in communication with one another. The first portion 212*a* may taper from a first diameter located at the second end 206 to a second diameter such that the second diameter smaller than the first diameter. The first portion 212*a* may be tapered to form a Morse taper, although first portion 212*a* may be otherwise tapered. The second portion 212*b* may have a third diameter that is smaller than the first and second diameters. The third portion 212*c* may extend inwardly from the first end 204 and have a fourth diameter that is greater than the third diameter.

In some embodiments, an external engagement feature 214 may be disposed adjacent to the second end 206. The engagement element 214 may take a variety of forms, including one or more flats to facilitate engagement by a tool, such as a wrench. Other examples of engagement elements are disclosed in U.S. patent application Ser. No. 17/650,116, filed Feb. 2, 2022, the entirety of which is incorporated herein by reference. In some embodiments, the external engagement feature 214 may be omitted. Further, in some embodiments, the top component may include a cylindrical portion disposed between the first end 204 and the second end 206 such that the top component 202 may have a similar shape to the shape of the top component 102A shown in FIG. 2.

Figure 6:
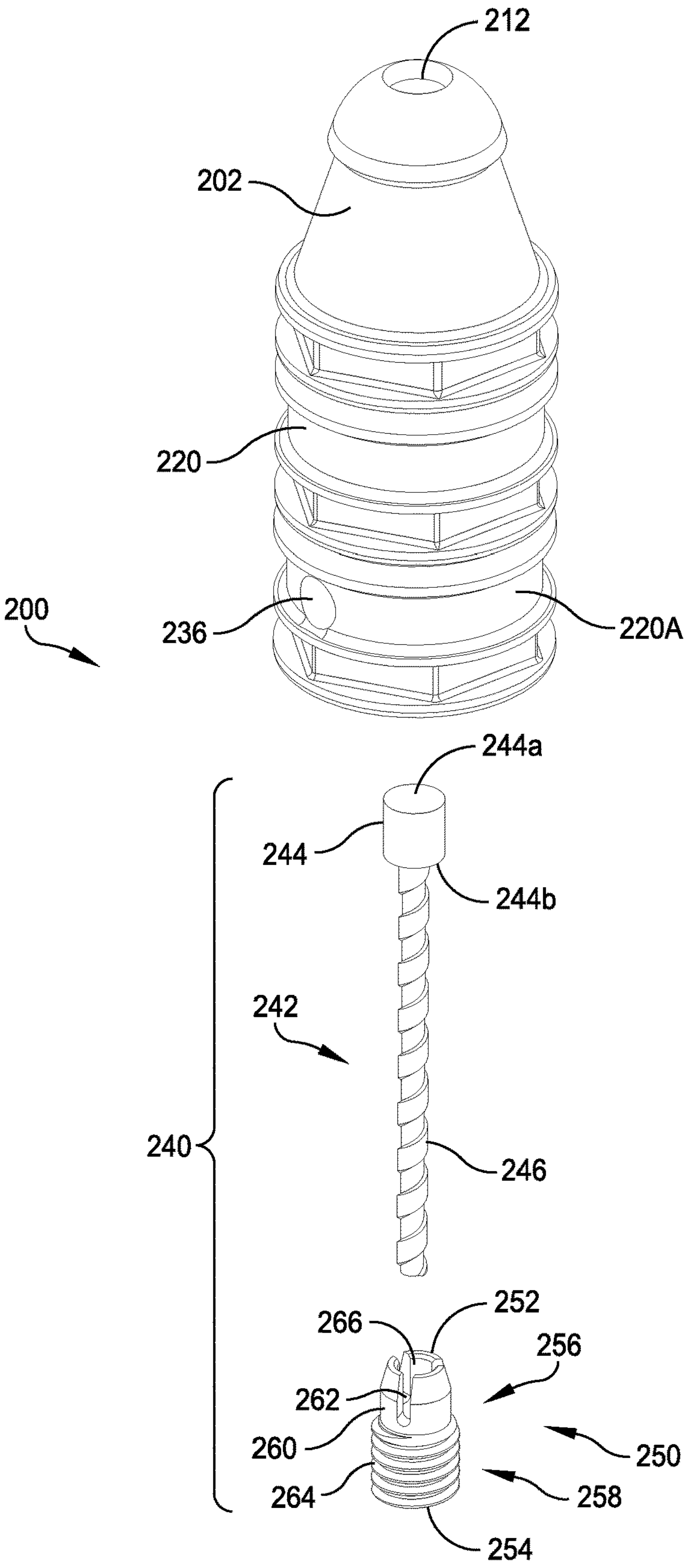
FIG. 6 is a partially exploded view of a stem of the assembled prosthesis illustrated in FIG. 5 in accordance with some embodiments.
Figure 7:
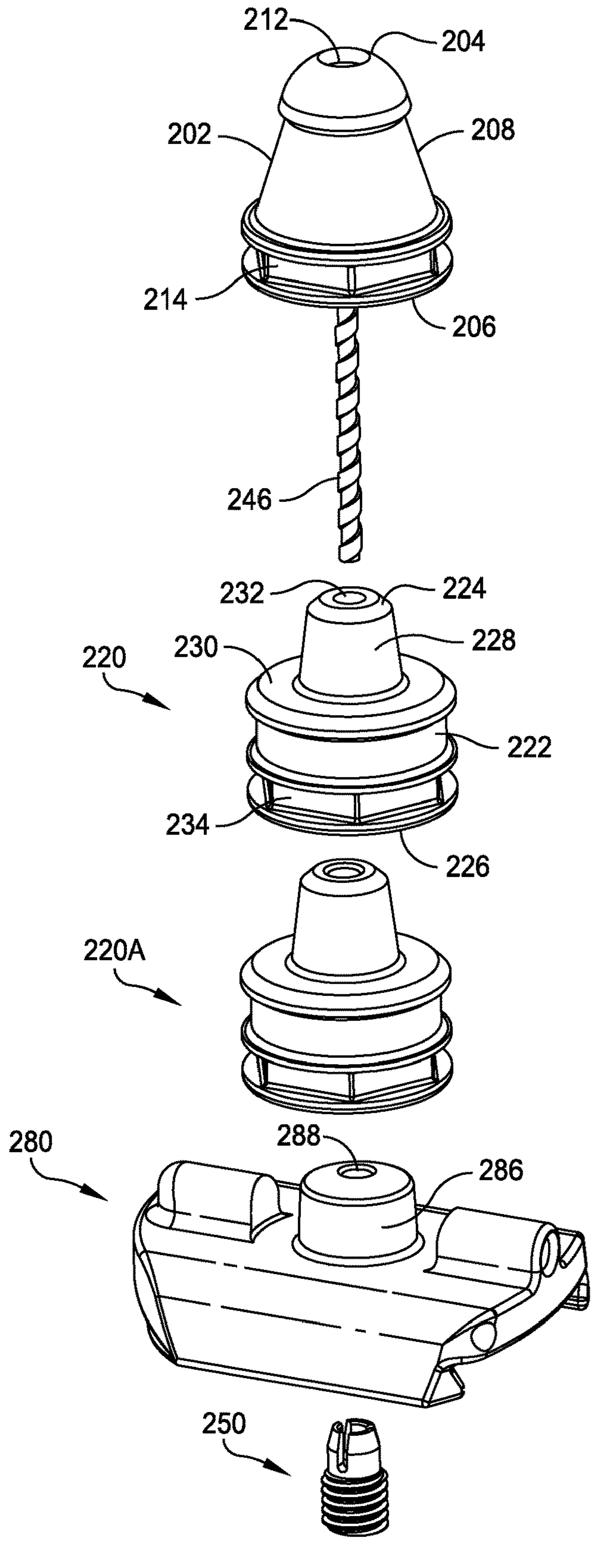
FIG. 7 is an exploded view of the stem of the assembled prosthesis illustrated in FIG. 5 in accordance with some embodiments.

Referring to FIGS. 6 and 9, component 220 may be a middle and/or trailing component that may be configured to be coupled to the top component 202. Component 220 may have a body 222 having a generally cylindrical shape and extend in a longitudinal direction from a first end 224 to a second end 226. In some embodiments, the length of the component 220 (e.g., a distance from the first end 224 to the second end 226) may be greater than a width (e.g., a diameter) of the component 220. However, it should be understood that length of the component 220 may be less than a width. In some embodiments, a kit may be provided in which a plurality of components 220 of differing sizes are provided in the kit.

The first end 224 of the component 220 may include a tapered region 228, which may also be referred to as a coupling region, that may be sized and configured to be received in at least a portion of the first portion 212*a* of the opening 112 of the top component 202. In some embodiments, the tapered region 228 extends from a shoulder 230 of the body 222. The tapered region 228 may be similar to the tapered region 128 described above. The second end 226 of the component 220 may define an opening 232 that extends inwardly towards first end 224. In some embodiments, the opening 232 may extend entirely through body 222. Opening 232 may include a first portion 232*a* and a second portion 232*b* that are in communication with one another. The first portion 232*a* may taper from a first diameter or width to a second diameter or width. The second diameter or width may be smaller than the first diameter or width. The first portion 232*a* of the opening 132 may be configured to form a tapered connection (e.g., a Morse taper) with another component, such as another component 220 and/or a tibia tray component, such as the tibia tray component 280 shown in FIGS. 5 and 9. The second portion 232*b* may have a generally cylindrical shape with a third diameter, which may be smaller than the first diameter or width and the second diameter or width. The second portion 232*b* may be sized and configured to receive a portion of a coupling member, such as the flexible shaft 246 of the coupling member 240.

An external engagement feature 234 may be disposed adjacent to the second end 226. The external engagement feature 234 may have a similar configuration (e.g., size and shape) to the engagement element 214 of the first component 202 such that the same tool may be used to engagement element 214 and engagement element 234. Accordingly, in some embodiments, the engagement element 234 may include one or more flats to facilitate engagement by a tool, such as a wrench. However, the engagement element may take a variety of forms, including the forms of the engagement elements disclosed in U.S. patent application Ser. No. 17/650,116. In some embodiments, the component 220 may be provided without an external engagement element 234. The outer surface of the body 222 of component 220 may include surface texturing to promote ingrowth/ongrowth, such as the surface texturing described above with respect to stem components stem components 120A, 120B.

Component 220A may have the same general configuration as component 220 described above, with the addition of a transverse hole 236. Transverse hole 236 may extend entirely through component 220A and be in communication with opening 232. Hole 236 may be sized and configured to receive a tool for disengaging a tapered coupling between component 236 and a protrusion of a tibia tray component as will be understood by one of ordinary skill in the art.

Coupling member 240 may be configured to couple the various components (e.g., the first component 202 and one or more second components 220) of the stem 200 together. In some embodiments, coupling member 240 also may be configured to couple the components of the stem 200 and the stem 200 to another component, such as a tibia tray component 280. Coupling member 240 may also be configured to apply a tension to or across one or more of the components 202, 220 as will be appreciated by one of ordinary skill in the art. In the example illustrated in FIG. 6, the coupling member 240 may include a tensioning wire 242 and a collet 250. Tensioning wire 242 may include a head portion 244 and a flexible shaft portion 246. In some embodiments, the head portion 244 may be a crimped sleeve on the flexible shaft portion 246, which may be a wire, cable, strand, filament, or other elongate flexible member. It should be further understood that the flexible shaft portion 246 may include a single member (e.g., strand or filament) or may include a plurality of strands or filaments, which may be disposed in a braided or unbraided configuration.

The head portion 244 may have a generally cylindrical shape extending from a free end 244*a* to a coupling end 244*b*. The head portion 244 may have a diameter that may be smaller than the diameter of the third portion 212*c* of the opening 212, but larger than a diameter of the second portion 212*b* such that head portion 244 may be received within the third portion 212*c* of the opening 212 defined by the top component 202. In some embodiments, the diameter of the head portion 244 is dimensioned such that the head portion 244 may be received in the third portion 212*c* of the opening 212 in a press-fit or slip-fit manner. Further, although the head portion 244 and the third portion 212*c* of opening 212 are shown and described as being cylindrical in shape, it should be understood that head portion 244 and third portion 212*c* of opening 212 may be tapered along their respective lengths or have other shapes.

The flexible shaft portion 246 may be coupled to the coupling end 244*b* of the head portion 244 and have a diameter that enables the flexible shaft portion to be received within the opening 212 defined by top component 202 and within the opening 232 defined by component 220. The length of the flexible shaft portion 246 may be sufficient so that the flexible shaft portion 246 may be received through a predetermined number of stem components, which may be a maximum possible number of stem components. In some embodiments, the flexible shaft portion 246 may have a length that enables the flexible shaft portion 246 to extend through a maximum possible number of stem components and through a tibia tray component. Providing the flexible shaft 246 with such a length may enable a kit or system to be provided with only a single size tensioning wire 242, which may reduce the number of components in a kit or system. However, it should be understood that multiple tensioning wires 242 may be provided in a kit or system such that a tensioning wire 242 may be provided for each possible size of stem that could be implanted, which may result in a reduction in the amount of material that may need to be removed from the flexible shaft portion 246 during installation.

In some embodiments, the tensioning wire 242 may be provided as a standalone component such that the tensioning wire 242 may be inserted through the top component 202 and any number of components 220 during surgery (or prior to surgery when removed from the kit). However, in some embodiments, the tensioning wire 242 may come preloaded in the top component 242.

Collet 250 may extend from a first end 252, which may be a leading end, to a second end 254, which may be a trailing end. Collet 250 may include a first portion 256 and a second portion 258. The first portion 256 may include a plurality of flexible arms 260 that are separated from one another by a slits 262. In some embodiments, the arms 260 may include a taper along their length to provide a cam surface as will be understood by one of ordinary skill in the art. The second portion 258 may include one or more threads 264. Collet 250 may also define a hole 266 that extends from the first end 252 to the second end 254. Hole 266 may be sized and configured to receive the flexible shaft portion 246 of the tensioning wire 242 and so the flexible arms 260 may lock onto the flexible shaft portion 246 when the flexible arms 260 are compressed.

Figure 5:
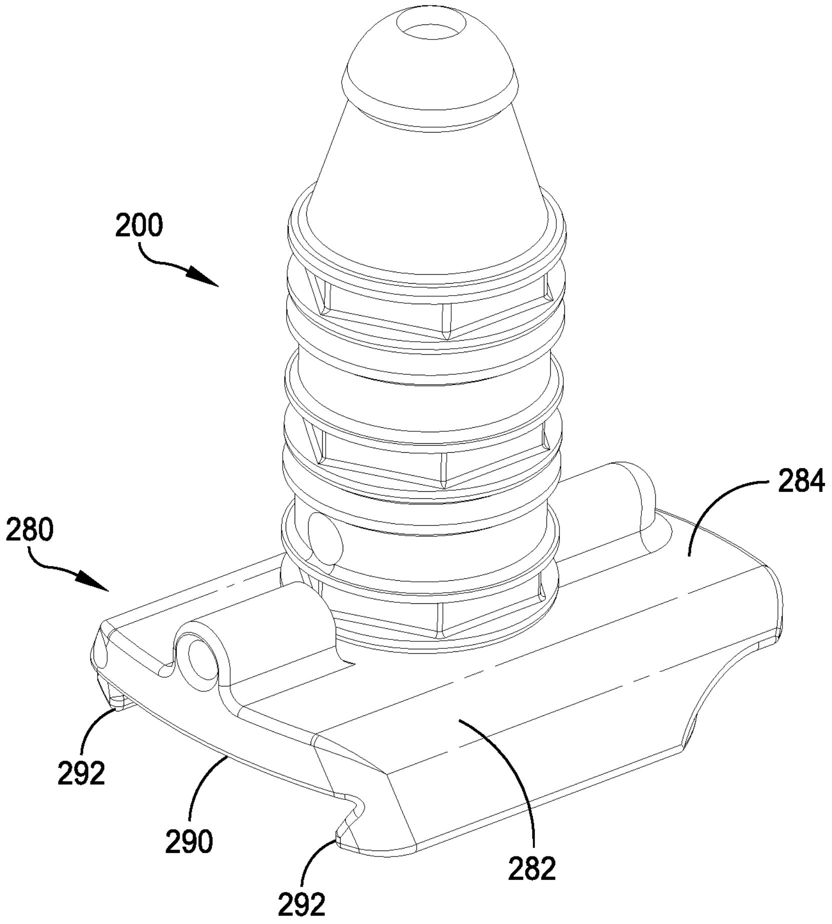
FIG. 5 is an isometric view of an assembled prosthesis in accordance with some embodiments.

Collet 250 may be sized and configured to be received within an opening 288 defined by tibia tray component 280. For example, the body 282 of tibia tray component 280 may include an upper surface 284 from which a protrusion 286 extends. The protrusion 286 may define the opening 288 that extends through the body 282 to an internal surface 290, which may be disposed between a pair of spaced apart rails 292, as best seen in FIGS. 5 and 9. Opening 288 may include a first portion 288*a* and a second portion 288*b*. First portion 288*a* may taper along its length and be configured to engage the cam surface of the flexible arms 260 of the collet 250 to facilitate locking of the collet 250 to the flexible shaft portion 246 of the tensioning wire 242. The second portion 288*b* of the opening 288 may include one or more threads configured to engage the one or more threads 264 of collet 250.

In use, the patient's anatomy may be prepared, such as by reaming an intramedullary canal in bone, such as is described in U.S. Pat. No. 7,534,246, which is incorporated by reference herein in its entirety. The tensioning wire 242 may be preloaded into stem component 202. If tensioning wire 242 is not preloaded into stem component 202, then the flexible shaft portion 246 may be inserted into the opening 212 such that the flexible shaft portion 246 is received first in the third portion 212*c*, then in the second portion 212*b* and the first portion 212*c*. With the tensioning wire 242 coupled to the first component 202, the first component 202 may be inserted into the intramedullary canal. In some embodiments, the first component 202 may be inserted into the intramedullary canal by inserting the first component 202 into a resected joint space formed between a tibia and a talus such that the first component enters the joint space in an anterior-to-posterior direction. The first component 202 may be engaged by a tool and pressed into the intramedullary canal.

A second component, such as component 220, may be coupled to the first component 202 in situ by inserting the component 220 into the resected joint space in an anterior-to-posterior direction. The flexible shaft portion 246 that extends from the first component 202 may be inserted into the opening 232 defined by the component 220. The component 220 may be pressed into engagement with the first component 202 by aligning the two components and inserting the tapered region 228 of the component 220 into the first portion 212*a* of the opening defined by the first component 202. The construct of the first component 202 and the second component 220 may be advanced farther into the intramedullary canal.

A third component, which may be component 220A, may be coupled to the construct of the first component 202 and second component 220 in situ. For example, the third component 220A may be inserted into the resected joint space in an anterior-to-posterior direction. The flexible shaft portion 246 that extends from the second end 226 of the component 220 may be inserted into the opening 232 defined by the component 220A such that at least a portion of the flexible shaft portion 246 extends from the second end 226 of component 220A. Component 220A may be pressed into engagement with the second component 220 by aligning the two components and inserting the tapered region 228 of component 220A into the first portion 232*a* of the opening 232 defined by component 220.

When a stem of a desired length has been achieved, the tibia tray component 280 may be coupled to the stem 200. For example, the tibia tray component 280 may be inserted into the resected joint space such that the protrusion 286 may be aligned with the opening 232 defined by the component 220A. The flexible shaft portion 246 may extend from the second end 226 of component 220A and be received in the opening 288 defined by the protrusion 286. The flexible shaft portion 246 also is inserted into the hole 266 defined by the collet 250, which may be preloaded into the tibia tray component 280 or separately coupled to the tibia tray component. A pair of pliers, vice grips, or other tool may be used to pull on the flexible shaft portion 246 of the tensioning wire 242 to compress the components of the stem 200 and the stem 200 onto the tibia tray component 280. The collet 250 may be rotated such that the threads 264 of the collet 250 engage the threaded portion 288*b* of the opening 288 defined by the tibia tray component 280. The advancement of the collet 250 into the opening 288 results in the flexible arms 260 of the collet being compressed and clamping onto the flexible shaft portion 246 to lock the construct together. Any excess portion of the flexible shaft portion 246 may be cut using a wire cutter, snips, or any other suitable tool.

Figure 10:
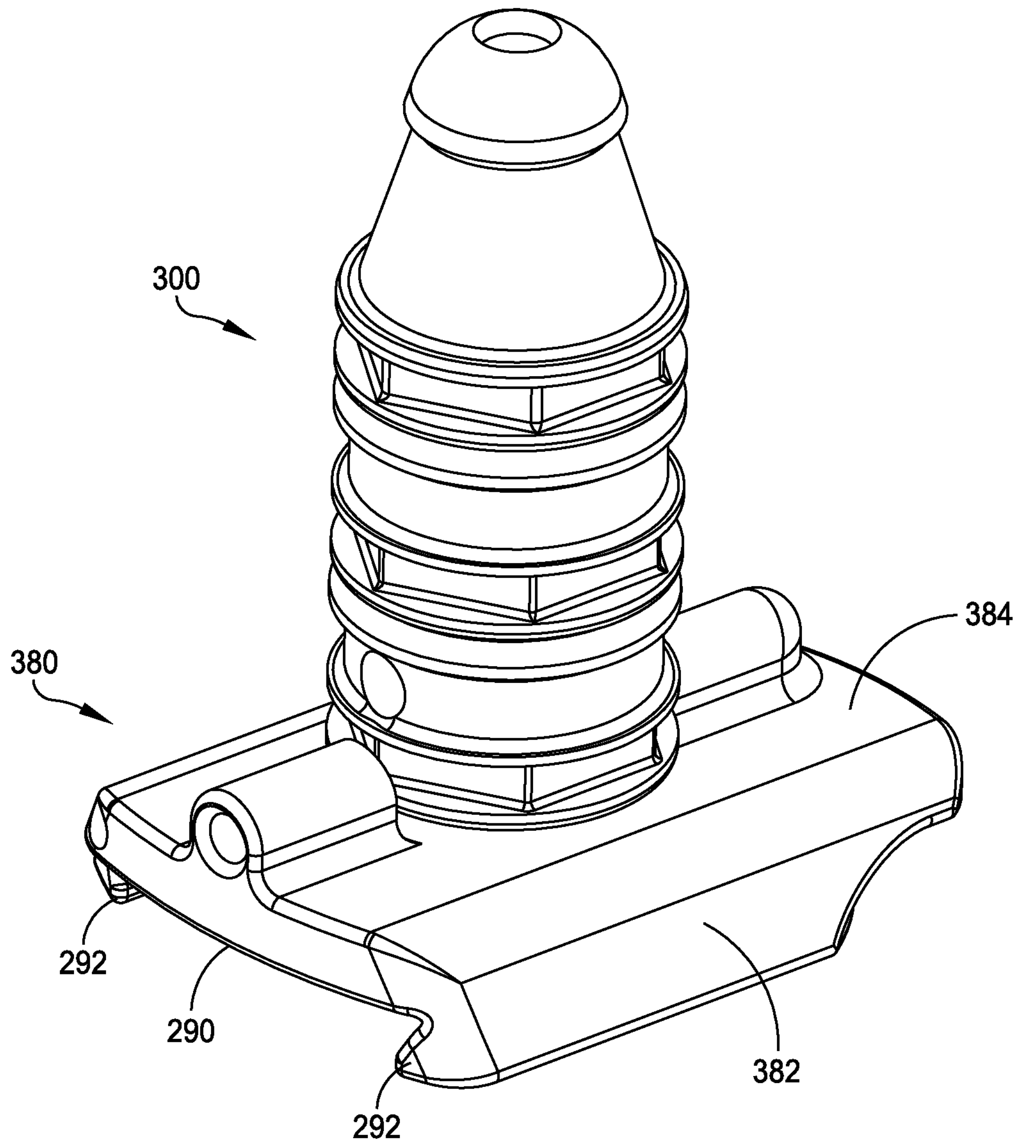
FIG. 10 is an isometric view of another example of an assembled prosthesis in accordance with some embodiments.
Figure 11:
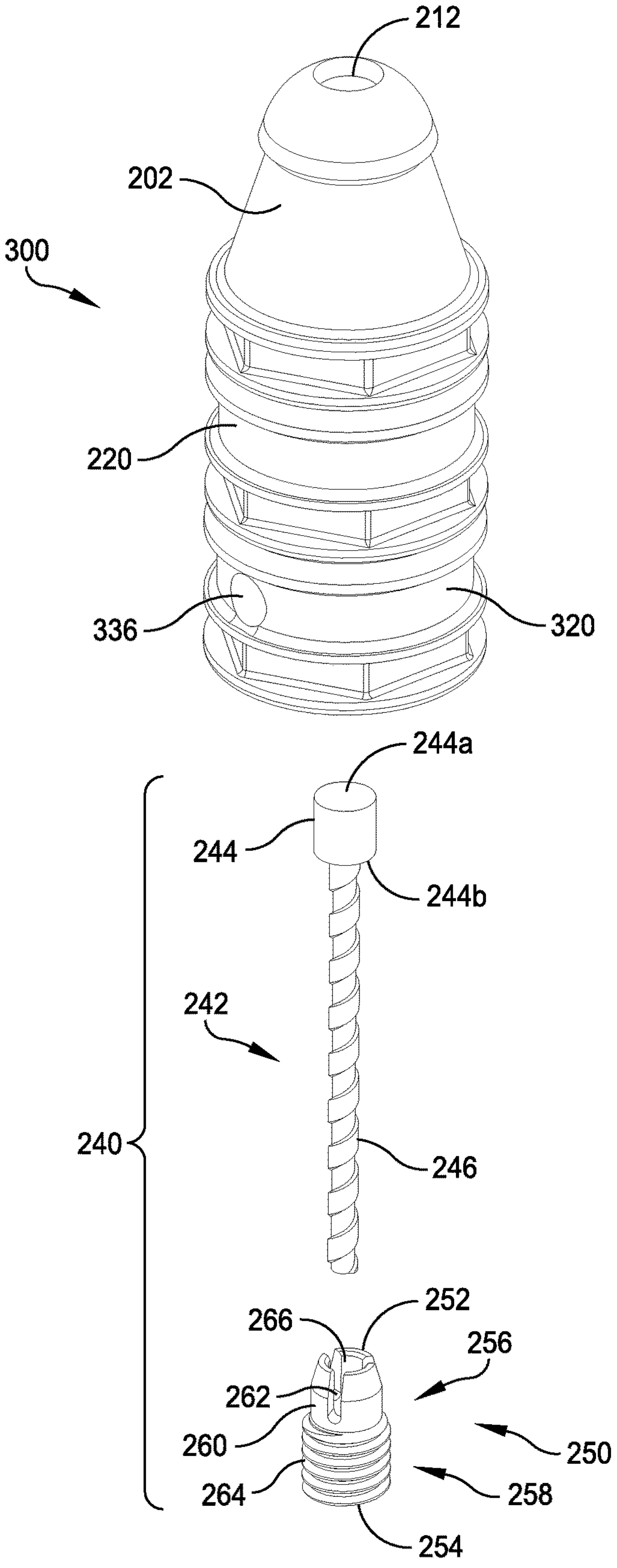
FIG. 11 is a partially exploded view of a stem of the assembled prosthesis illustrated in FIG. 10 in accordance with some embodiments.
Figure 12:
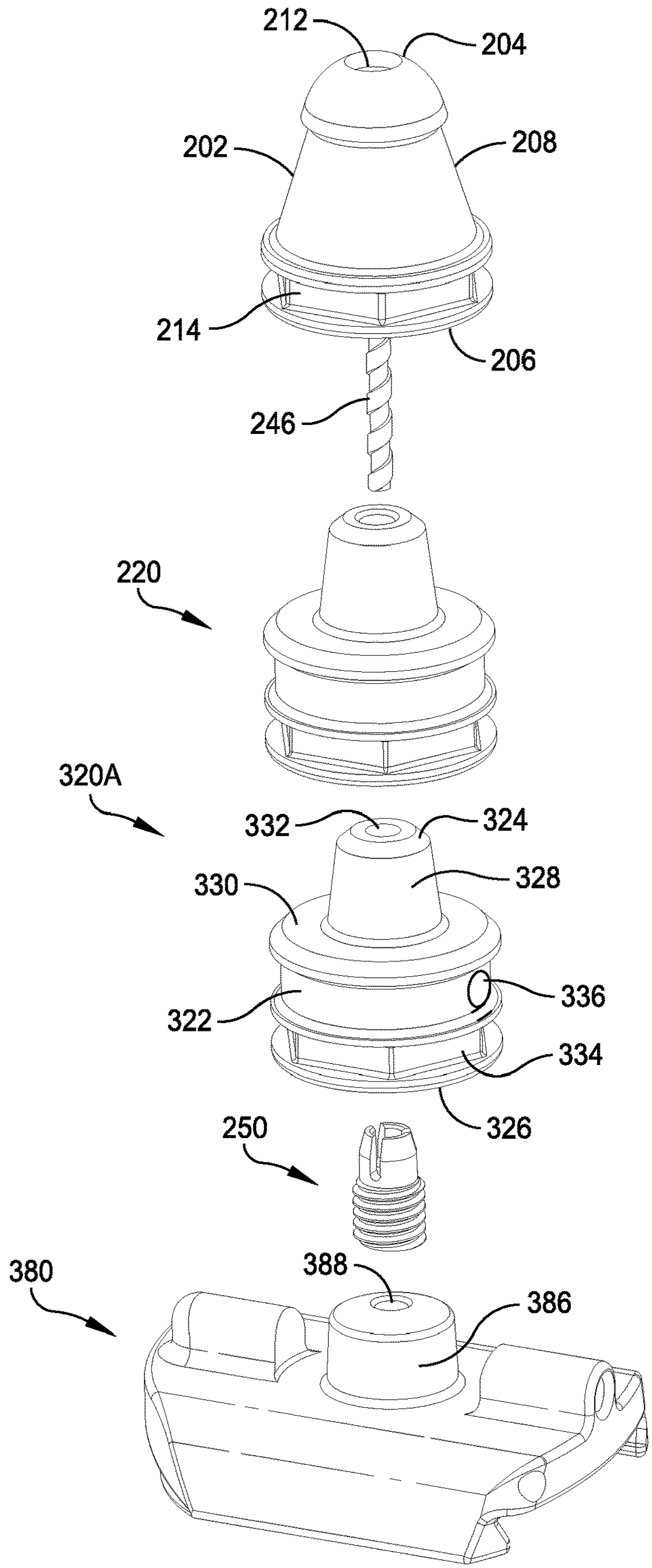
FIG. 12 is an exploded view of the stem of the assembled prosthesis illustrated in FIG. 10 in accordance with some embodiments.

FIGS. 10-14 illustrate another example of a prosthesis that may include a stem and a tibia tray component. Stem 300 may be configured so that each of the stem components may be locked together by a coupling member 240 and be separately coupled to a tibia tray component 380. Stem 300 may include a first component 202 and a second component 220, as described above, and a third component 320. As best seen in FIGS. 11-12, stem component 320 may have a body 322 having a generally cylindrical shape and extend in a longitudinal direction from a first end 324 to a second end 326. In some embodiments, the length of the component 320 (e.g., a distance from the first end 324 to the second end 326) may be greater than a width (e.g., a diameter) of the component 320. However, it should be understood that length of the component 320 may be less than a width. In some embodiments, a kit may be provided in which a plurality of components 320 of differing sizes are provided in the kit.

The first end 324 of the component 320 may include a tapered region 328, which may also be referred to as a coupling region, that may be sized and configured to be received in at least a portion of the first portion 212*a* of the opening 212 of the top component 202 or in the first portion 232*a* of the opening 232 of component 220. In some embodiments, the tapered region 328 extends from a shoulder 330 of the body 322. The tapered region may have a conical shape, pyramidal shape, or other shaped in the same or similar manner to the tapered region 128 described above. The second end 326 of the component 320 may define an opening 332 that extends inwardly towards first end 324. In some embodiments, the opening 332 may extend entirely through body 322. Opening 332 may include a first portion 332*a*, a second portion 332*b*, and a third portion 332*c* that are in communication with one another. The first portion 332*a* may be tapered to provide a Morse tapered connection with another component, such as another component of the stem or with a tibia stem component, including tibia stem component 380. The second portion 332*b* may be a threaded portion and include one or more threads sized and configured to engage the threads 264 of collet 250. The third portion 332*c* may have a generally cylindrical shape that tapers along its length such that the third portion 332*c* may be configured to engage the flexible arms 260 of collet 250 to facilitate locking of the collet 250 to the flexible shaft portion 246 of the tensioning wire 242.

An external engagement feature 334 may be disposed adjacent to the second end 326. The external engagement feature 334 may have a similar configuration (e.g., size and shape) to the engagement element 214 of the first component 202 and engagement element 234 of component 220 such that the same tool may be used to engage engagement elements 214, 234, 334. Accordingly, in some embodiments, the engagement element 334 may include one or more flats to facilitate engagement by a tool, such as a wrench. However, the engagement element may take a variety of forms, including the forms of the engagement elements disclosed in U.S. patent application Ser. No. 17/650,116. In some embodiments, the component 320 may be provided without an external engagement element 234. The outer surface of the body 322 of component 320 may include surface texturing to promote ingrowth/ongrowth, such as the surface texturing described above with respect to stem components stem components 120A, 120B. Component 320 may also include a transverse hole 336 that extends through the entirety of component 320 and is sized and configured to receive a tool for disengaging a tapered connection. Although hole 336 is shown as extending through the entirety of component 320, it should be understood that hole 336 may extend only partially through component 320.

Figure 14:
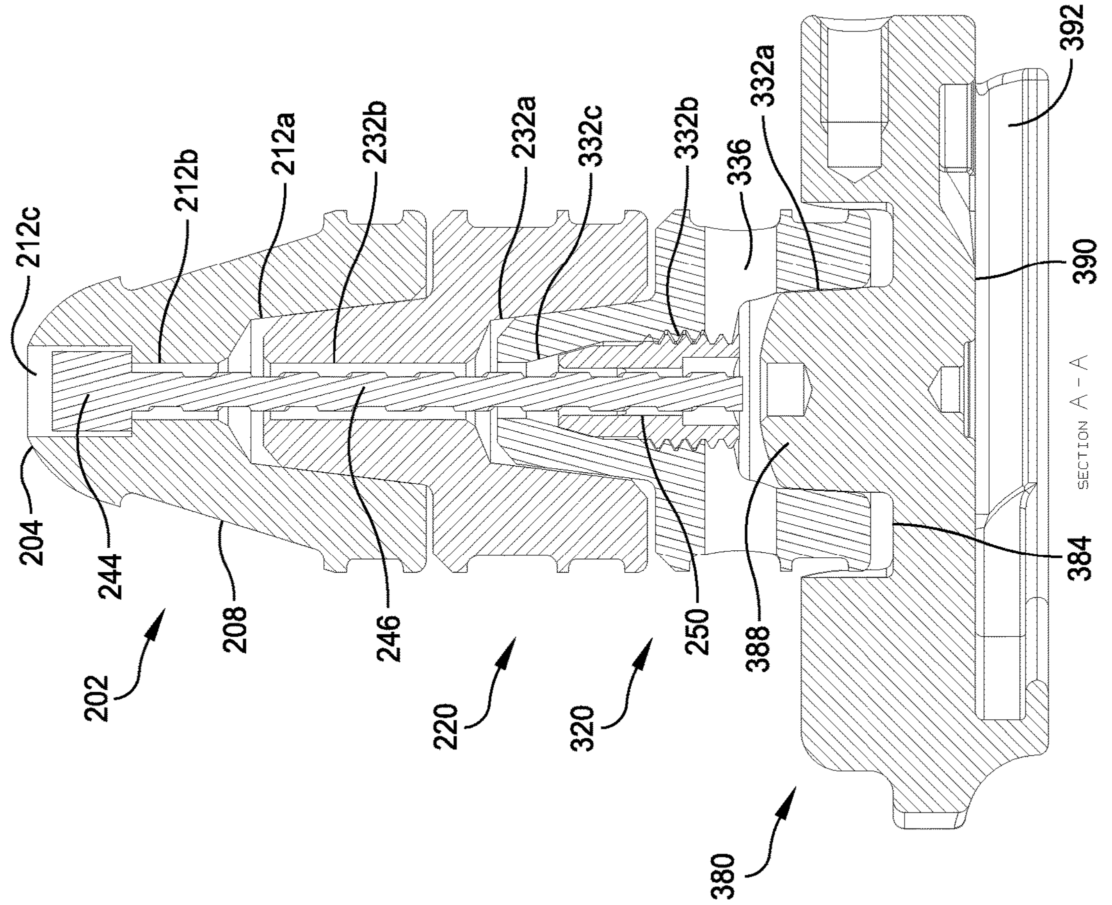
FIG. 14 is a cross-sectional view taken along line A-A in FIG. 13 in accordance with some embodiments.
Figure 13:
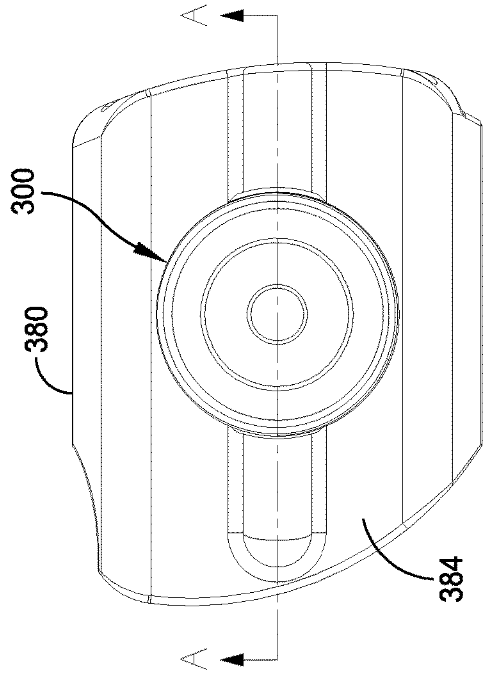
FIG. 13 is a top side view of the assembled prosthesis illustrated in FIG. 10 in accordance with some embodiments.

As best seen in FIGS. 10 and 14, tibia tray component 380 may have a body 382 with an upper surface 384 from which a protrusion 386 extends. In some embodiments, protrusion 386 may be provided without an opening that extends entirely through the protrusion 386. Protrusion 386 may be tapered along its length and sized such that protrusion 386 may be configured to be at least partially received in the first portion 332*a* of the opening 332 defined by the component 320. Tibia tray component may include an inner surface 390 between a pair of spaced apart rails 392, which may be sized and configured to receive an artificial articular surface.

In use, the patient's anatomy may be prepared, such as by reaming an intramedullary canal in bone. The tensioning wire 242 may be preloaded into stem component 202. If tensioning wire 242 is not preloaded into stem component 202, then the flexible shaft portion 246 may be inserted into the opening 212 such that the flexible shaft portion 246 is received first in the third portion 212*c*, then in the second portion 212*b* and the first portion 212*c*. With the tensioning wire 242 coupled to the first component 202, the first component 202 may be inserted into the intramedullary canal. In some embodiments, the first component 202 may be inserted into the intramedullary canal by inserting the first component 202 into a resected joint space formed between a tibia and a talus such that the first component enters the joint space in an anterior-to-posterior direction. The first component 202 may be engaged by a tool and pressed into the intramedullary canal.

A second component, such as component 220, may be coupled to the first component 202 in situ by inserting the component 220 into the resected joint space in an anterior-to-posterior direction. The flexible shaft portion 246 that extends from the first component 202 may be inserted into the opening 232 defined by the component 220. The component 220 may be pressed into engagement with the first component 202 by aligning the two components and inserting the tapered region 228 of the component 220 into the first portion 212*a* of the opening defined by the first component 202. The construct of the first component 202 and the second component 220 may be advanced farther into the intramedullary canal.

A third component, such as component 320, may be coupled to the construct of the first component 202 and second component 220 in situ. For example, the third component 320 may be inserted into the resected joint space in an anterior-to-posterior direction. The flexible shaft portion 246 that extends from the second end 226 of the component 220 may be inserted into the opening 332 defined by the component 320 such that at least a portion of the flexible shaft portion 246 extends from the second end 326 of component 320. If collet 250 is coupled to component 320 when the component 320 is inserted into the resected joint space, then the flexible shaft portion 246 may be received in the hole 266 defined by the collet 250. If collet 250 is not coupled to component 320 when the component 320 is inserted into the resected joint space, then the collet 250 may be coupled to component 320 in situ by inserting the flexible shaft portion 246 into the hole 266 defined by the collet 250 and inserting collet 250 into the opening 332 defined by component 320.

The stem may be compressed and locked together by using coupling member 240. For example, tension may be applied to tensioning wire 242 using a pair of pliers, vice grips, or other suitable tool. Pulling on the flexible shaft portion 246 while applying pressure to the second end 326 of stem component 320 compresses the stem components together. The collet 250 may be rotated such that the threads 264 of collet 250 engage the threaded portion 332*a* of the opening defined by component 320. The advancement of the collet 250 into the opening 332 defined by component 320 results in the flexible arms 260 of the collet 250 being compressed and clamping onto the flexible shaft portion 246 to lock the stem components together. Any excess portion of the flexible shaft portion 246 may be cut using a wire cutter, snips, or any other suitable tool.

The tibia tray component 380 may be coupled to the stem 300. For example, the tibia tray component 380 may be inserted into the resected joint space such that the protrusion

386 may be aligned with the opening 232 defined by the component 320 of the stem 300. The protrusion 386 of the tibia tray component 380 is pressed into the first portion 332*a* to form a tapered connection. An artificial articular surface may be coupled to the tibia tray component 380 as will be understood by one of ordinary skill in the art.

The tibia stem component and/or the tibia tray component in the various embodiments of the prosthesis disclosed herein can be made of any total joint material of materials commonly used in the prosthetic art, including, but not limited to, metals, ceramics, titanium, titanium alloys, tantalum, chrome cobalt, surgical steel, polyethylene, absorbable polymer, or any other total joint replacement metal and/or ceramic. In some embodiments, the tibia stem component and/or the tibia tray component can comprise a coating of 3D printed Biofoam™, Adaptis™, porous metal, sintered glass, artificial bone, any uncemented metal or ceramic surface, or a combination thereof that would promote bony in-growth. As noted above, other surface texturing, including grit blasting, may be applied to the outer surfaces of the stem and/or tibia tray component to facilitate bony ingrowth/ongrowth. The tibia stem component and/or the tibia tray component can further be covered with one or more coatings such as antimicrobial, antithrombotic, and osteoinductive agents, or a combination thereof. In embodiments where the above-mentioned porous coating is provided, these agents can further be carried in a biodegradable carrier material with which the pores in the porous coating can be impregnated.

Although the examples of the inventive structures illustrated herein are exemplified as tibia stem and tray components of an ankle replacement prosthesis, the inventive structures are equally applicable in other physical joints in human or animal skeleton.

It will be understood that the foregoing description is of exemplary embodiments of this invention, and that the invention is not limited to the specific forms shown. Modifications may be made in the design and arrangement of the elements without departing from the scope of the invention.

What is claimed is:

1. An ankle prosthesis, comprising:

a tibia stem component comprising a leading end, a trailing end, and a longitudinal axis defined therethrough, wherein the tibia stem component comprises:

a first component having a first body extending from a first end to a second end, the second end of the first component defining a first opening that extends inwardly toward the first end of the first component, the first opening including a first portion having a first diameter, a second portion having a second diameter that is different from the first diameter, and a third portion;

a second component having a second body extending from a first end to a second end, the first end of the second body including a conical tapered region extending from a shoulder of the second body, the conical tapered region sized and configured to be at least partially received in the first portion of the first opening, the second body defining a second opening that extends through the second body from the first end of the second body to the second end of the second body; and a coupling member configured to couple the first component and the second component by compressing the first component and the second component, the coupling member including a tensioning wire comprising a head portion and a flexible shaft portion, the head portion sized and configured to be received within the third portion of the first opening, and a collet defining a third opening and including a plurality of flexible arms, the third opening sized and configured to receive the flexible shaft portion of the tensioning wire.

2. The prosthesis of claim 1, wherein:

the second portion of the first opening is located between the first portion of the first opening and the third portion of the first opening.

3. The prosthesis of claim 1, wherein the second opening defined by the second component includes a first portion and a second portion.

4. The prosthesis of claim 3, wherein:

the first portion of the second opening includes at least one thread sized and configured to be engaged by a thread disposed on an outer surface of the collet, and the second portion of the second opening includes a taper configured to engage the plurality of flexible arms.

5. The prosthesis of claim 3, wherein:

the first portion of the second opening includes a taper sized and configured to engage a protrusion of another component.

6. The prosthesis of claim 5, further comprising a third component having a third body, the third body including:

a pair of spaced apart rails, and a protrusion extending from an upper surface of the third body, the protrusion of the third body sized and configured to be received in the first portion of the second opening.

7. The prosthesis of claim 6, wherein the third body defines a fourth opening sized and configured to receive the collet therein.

8. The prosthesis of claim 7, wherein the fourth opening defined by the third body includes a first portion and a second portion, the first portion of the fourth opening including at least one thread configured to engage at least one thread disposed on an outer surface of the collet, and the second portion of the fourth opening including a taper configured to engage the plurality of flexible arms.

9. The prosthesis of claim 1, wherein the first portion includes at least one anti-rotation feature extending from an outer surface of the first body.

10. The prosthesis of claim 9, wherein the at least one anti-rotation feature includes a plurality of fins extending from the first end of the first body toward the second end of the first body.

11. The prosthesis of claim 1, wherein an outer surface of the first body includes surface texturing to promote bone ingrowth/ongrowth.

12. The prosthesis of claim 11, wherein the surface texturing includes at least one groove formed in the outer surface of the first body.

13. The prosthesis of claim 12, wherein the at least one groove includes at least one circumferential groove.

14. The prosthesis of claim 12, wherein the at least one groove includes at least one helical groove.

15. The prosthesis of claim 14, wherein the at least one groove includes at least one circumferential groove.

16. The prosthesis of claim 11, wherein the surface texturing includes a texture formed by grit blasting.

17. The prosthesis of claim 1, wherein the first body includes an elongate cylindrical section disposed between the first end of the first body and the second end of the first body.

18. An ankle prosthesis, comprising:

a tibia stem component comprising a leading end, a trailing end, and a longitudinal axis defined therethrough, wherein the tibia stem component comprises:

a first component having a first body extending from a first end to a second end, an outer surface of the first body including a plurality of helical grooves and a plurality of circumferential grooves formed therein, the second end of the first component defining a first opening extending inwardly toward the first end of the first component, the first opening including a first portion, a second portion, and a third portion;

a second component having a second body extending from a first end to a second end, the first end of the second body including a conical tapered region extending from a shoulder of the second body, the conical tapered region sized and configured to be at least partially received in the first portion of the first opening, the second body defining a second opening that extends through the second body from the first end to the second end of the second body; and a coupling member including a tensioning wire comprising a head portion and a flexible shaft portion, the head portion sized and configured to be received within the third portion of the first opening, and a collet defining a third opening and including a plurality of flexible arms, the third opening sized and configured to receive the flexible shaft portion of the tensioning wire.

19. The prosthesis of claim 18, wherein the plurality of circumferential grooves intersect the plurality of helical grooves.

20. The prosthesis of claim 18, further comprising a third component having a third body extending from a first end to a second end, the second end of the third body defining a fourth opening, the fourth opening including a first portion having at least one thread configured to engage at least one thread disposed on an outer surface of the collet, and a second portion including a taper configured to engage the plurality of flexible arms.

21. The prosthesis of claim 20, wherein the first end of the third body includes a tapered region sized and configured to be received in the second opening defined by the second component.

22. The prosthesis of claim 20, further comprising a fourth component having a fourth body including a pair of spaced apart rails, and a conical protrusion extending from an upper surface of the fourth body, the conical protrusion sized and configured to be at least partially received in the fourth opening defined by the third body.

* * * * *